United States Patent
Guldberg et al.

(10) Patent No.: US 9,452,049 B2
(45) Date of Patent: Sep. 27, 2016

(54) SYSTEMS AND METHODS TO AFFECT ANATOMICAL STRUCTURES

(75) Inventors: Robert E. Guldberg, Marietta, GA (US); Yash M. Kolambkar, Mableton, GA (US); Dietmar W. Hutmacher, Kenmore Hills (AU)

(73) Assignees: GEORGIA TECH RESEARCH CORPORATION, Atlanta, GA (US); QUEENSLAND UNIVERSITY OF TECHNOLOGY, Brisbane, Queensland (AU)

( * ) Notice: Subject to any disclaimer, the term of this patent is extended or adjusted under 35 U.S.C. 154(b) by 704 days.

(21) Appl. No.: 12/625,069

(22) Filed: Nov. 24, 2009

(65) Prior Publication Data
US 2010/0168771 A1   Jul. 1, 2010

Related U.S. Application Data

(60) Provisional application No. 61/117,399, filed on Nov. 24, 2008.

(51) Int. Cl.
*A61F 2/30* (2006.01)
*A61F 2/28* (2006.01)
(Continued)

(52) U.S. Cl.
CPC .......... *A61F 2/2846* (2013.01); *A61L 27/3804* (2013.01); *A61L 27/3834* (2013.01); *A61L 27/52* (2013.01); *A61L 27/54* (2013.01); *A61L 27/56* (2013.01); *A61L 31/146* (2013.01);
(Continued)

(58) Field of Classification Search
CPC ............. A61F 2002/3084; A61F 2002/30028; A61F 2/30767; A61F 2002/30838; A61F 2002/3093; A61F 2002/30011; A61F 2002/3092; A61F 2/0063; A61F 2002/0068; A61B 17/0057
USPC .............................. 623/1.46, 22.33; 606/151
See application file for complete search history.

(56) References Cited

U.S. PATENT DOCUMENTS

| | | |
|---|---|---|
| 5,660,225 A | 8/1997 | Saffran |
| 5,676,699 A | 10/1997 | Gogolewski et al. |

(Continued)

FOREIGN PATENT DOCUMENTS

| | | | | |
|---|---|---|---|---|
| EP | WO2006096791 | * | 3/2006 | ............... A61F 2/02 |
| WO | 2006096791 A2 | | 9/2006 | |

(Continued)

OTHER PUBLICATIONS

International Search Report and Written Opinion dated Mar. 23, 2010 for related PCT Application No. PCT/US2009/065754.
(Continued)

*Primary Examiner* — Christian Sevilla
*Assistant Examiner* — Seema Mathew
(74) *Attorney, Agent, or Firm* — Troutman Sanders LLP; Ryan A. Schneider; Troy S. Kleckley

(57) ABSTRACT

Systems and method to affect anatomical structures is disclosed. The systems and method can be used to regenerate bone. The system can comprise a nanofiber mesh configured to substantially conform to an anatomical structure, wherein at least a portion of the nanofiber mesh defines a fillable space. The system can comprise a carrier substance comprising an active agent, such as a bone morphogenetic protein, The carrier substance can be disposed within the fillable space.

12 Claims, 19 Drawing Sheets

(51) Int. Cl.
  *A61L 27/38* (2006.01)
  *A61L 27/52* (2006.01)
  *A61L 27/54* (2006.01)
  *A61L 27/56* (2006.01)
  *A61L 31/14* (2006.01)
  *A61L 31/16* (2006.01)
  *A61F 2/00* (2006.01)

(52) U.S. Cl.
  CPC ............. *A61L 31/16* (2013.01); *A61F 2/3094* (2013.01); *A61F 2/30767* (2013.01); *A61F 2002/0068* (2013.01); *A61F 2002/285* (2013.01); *A61F 2002/2817* (2013.01); *A61F 2002/2825* (2013.01); *A61F 2002/30028* (2013.01); *A61F 2002/30075* (2013.01); *A61F 2002/3084* (2013.01); *A61F 2002/3092* (2013.01); *A61F 2002/30235* (2013.01); *A61F 2002/30838* (2013.01); *A61F 2002/30914* (2013.01); *A61F 2210/0061* (2013.01); *A61F 2230/0069* (2013.01); *A61F 2240/001* (2013.01); *A61F 2310/00365* (2013.01); *A61L 2300/414* (2013.01); *A61L 2400/06* (2013.01); *A61L 2400/12* (2013.01); *A61L 2430/02* (2013.01)

(56) References Cited

U.S. PATENT DOCUMENTS

| | | | | |
|---|---|---|---|---|
| 6,027,744 | A * | 2/2000 | Vacanti | A61F 2/28 424/426 |
| 6,328,765 | B1 | 12/2001 | Hardwick et al. | |
| 6,391,059 | B1 * | 5/2002 | Lemperle et al. | 623/23.5 |
| 6,409,764 | B1 | 6/2002 | White et al. | |
| 6,461,385 | B1 | 10/2002 | Gayer et al. | |
| 6,712,851 | B1 | 3/2004 | Lemperle et al. | |
| 6,719,793 | B2 | 4/2004 | McGee | |
| 6,942,873 | B2 | 9/2005 | Russell et al. | |
| 8,690,957 | B2 * | 4/2014 | Olson, Jr. | A61F 2/30907 623/22.21 |
| 8,883,195 | B2 * | 11/2014 | Bagga | A61L 27/56 424/423 |
| 8,889,178 | B2 * | 11/2014 | Bagga | A61L 27/56 424/423 |
| 2002/0082623 | A1 * | 6/2002 | Osther et al. | 606/151 |
| 2003/0003270 | A1 * | 1/2003 | Wheatley | B29C 73/10 428/137 |
| 2003/0100944 | A1 * | 5/2003 | Laksin | A61L 27/18 623/1.44 |
| 2005/0043733 | A1 | 2/2005 | Eisermann et al. | |
| 2005/0221072 | A1 * | 10/2005 | Dubrow | A61F 2/30767 428/292.1 |
| 2005/0250895 | A1 * | 11/2005 | Baker | B82Y 30/00 524/496 |
| 2006/0095137 | A1 | 5/2006 | Chung et al. | |
| 2007/0071790 | A1 * | 3/2007 | Ameer | A61L 27/18 424/423 |
| 2007/0141114 | A1 * | 6/2007 | Muisener | C09D 5/1693 424/427 |
| 2007/0142916 | A1 * | 6/2007 | Olson, Jr. | A61F 2/30907 623/17.11 |
| 2007/0150061 | A1 * | 6/2007 | Trieu | 623/17.12 |
| 2007/0282247 | A1 | 12/2007 | Desai et al. | |
| 2008/0208358 | A1 | 8/2008 | Bellamkonda et al. | |
| 2009/0123700 | A1 * | 5/2009 | Conley | A41D 31/02 428/152 |
| 2009/0324680 | A1 * | 12/2009 | Reneker | A61L 31/042 424/423 |
| 2011/0035023 | A1 * | 2/2011 | Maquet | A61L 27/20 623/23.65 |
| 2011/0125170 | A1 * | 5/2011 | Hoke | A61B 17/1128 606/152 |
| 2012/0040581 | A1 * | 2/2012 | Kim | C04B 35/62218 442/330 |
| 2012/0171257 | A1 * | 7/2012 | Inanc | A61L 27/18 424/400 |
| 2013/0103137 | A1 * | 4/2013 | Asano | A61M 1/3655 623/1.35 |
| 2013/0138155 | A1 * | 5/2013 | Hoornaert | A61L 31/146 606/283 |
| 2013/0150763 | A1 * | 6/2013 | Mirzaei | A61L 15/225 602/43 |
| 2014/0276330 | A1 * | 9/2014 | Costa | A61F 5/0076 604/8 |
| 2015/0298068 | A1 * | 10/2015 | Park | B01D 39/00 210/435 |

FOREIGN PATENT DOCUMENTS

| | | | | |
|---|---|---|---|---|
| WO | | 2008070186 A2 | 6/2008 | |
| WO | WO | 2008070186 A2 * | 6/2008 | ............... A61F 2/02 |

OTHER PUBLICATIONS

Gugala et al.; Healing of Critical-Size Segmental Bone Defects in the Sheep Tibiae Using Bioresorbable Polylactide Membranes; Injury, Int'l J. Care Injured; 33 (2002); pp. 71-76.

Oest et al.; Quantitative Assessment of Scaffold and Growth Factor-Mediated Repair of Critically Sized Bone Defects; J.Orthopaedic Res.; (2007); pp. 1-10.

Simmons et al.; Dual Growth Factor Delivery and Controlled Scaffold Degradation Enhance in vivo Bone Formation by Transplanted Bone Marrow Stromal Cells; Bone; 35; (2004); pp. 562-569.

Sill et al., "Electrospinning: Applications in drug delivery and tissue engineering," Biomaterials, Elsevier Science Publishers BV., Barking, GB, vol. 29, No. 13, pp. 1989-2006; Feb. 20, 2008.

Extended European Search Report in related European Application No. 09828381.5; mailed Oct. 20, 2014.

* cited by examiner

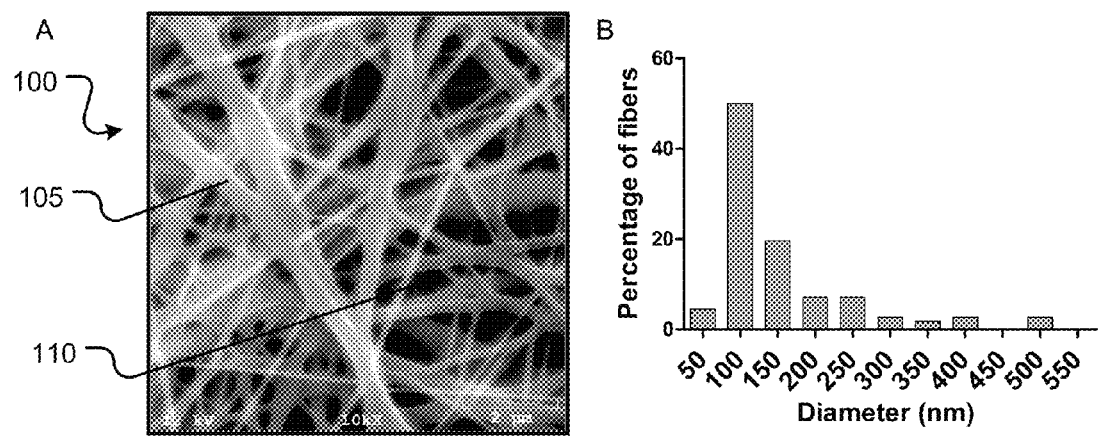
FIGURES 1A-B
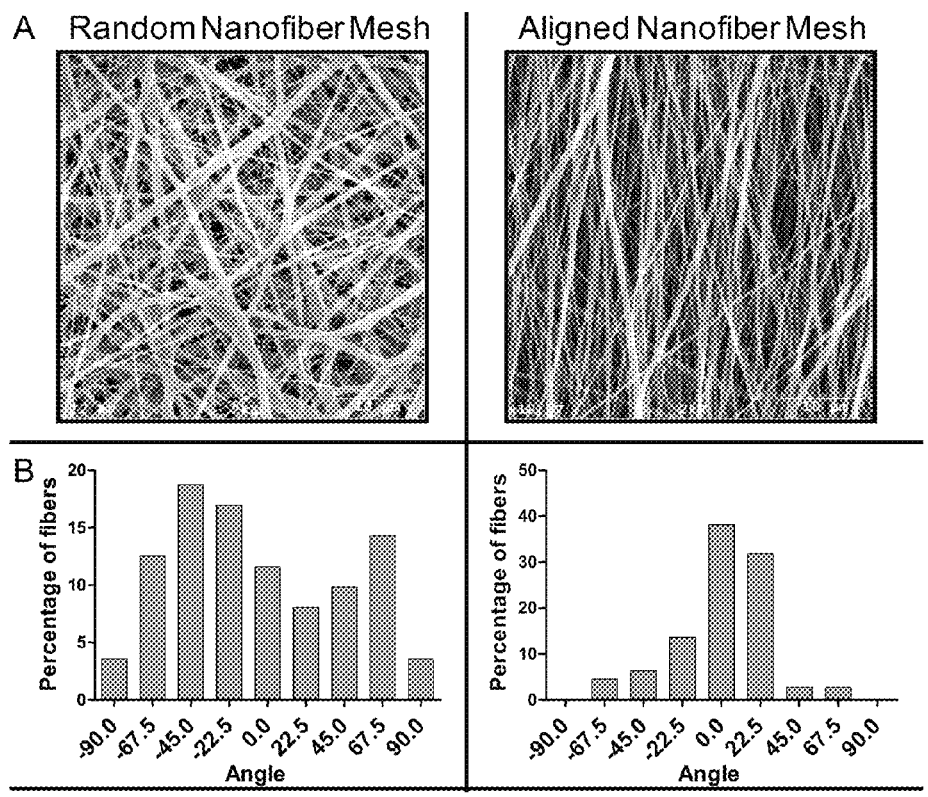
FIGURES 2A-B

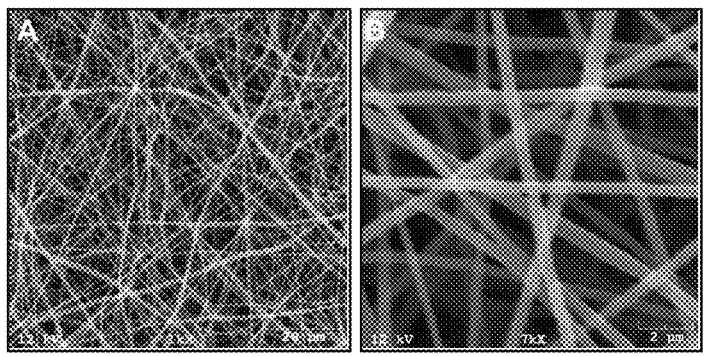
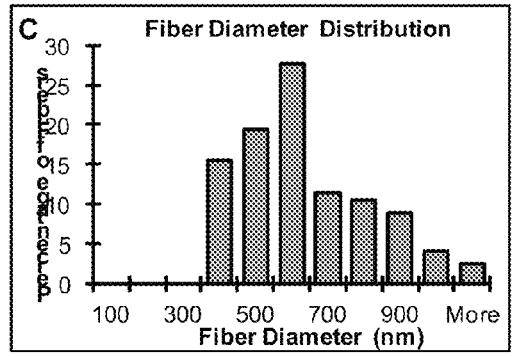
FIGURES 7A-C
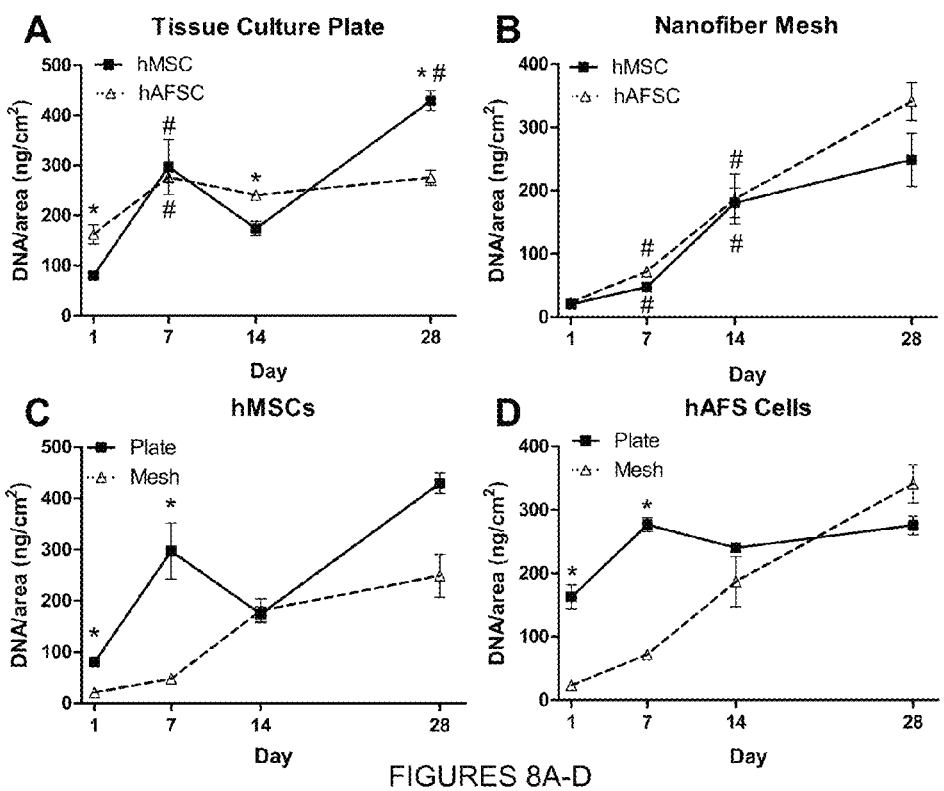
FIGURES 8A-D

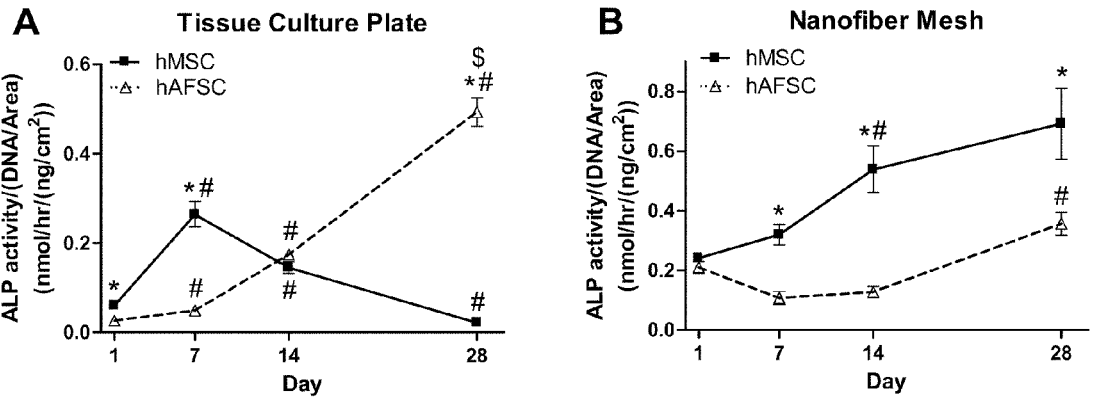
FIGURES 9A-B
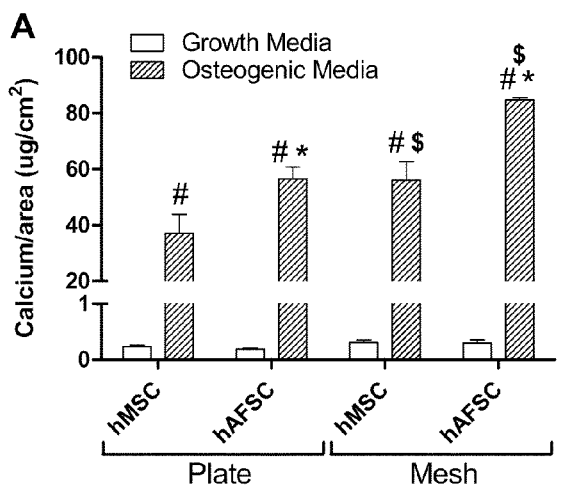
FIGURE 10
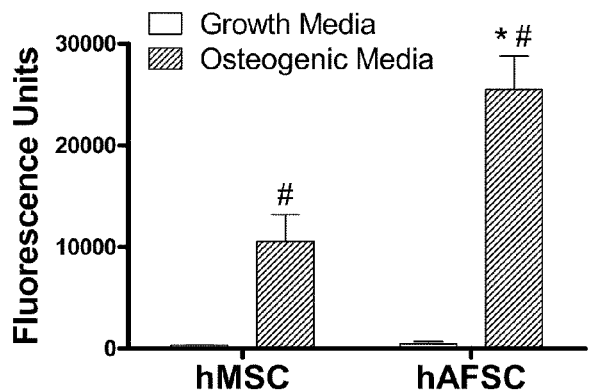
FIGURE 11

FIGURES 13A-B

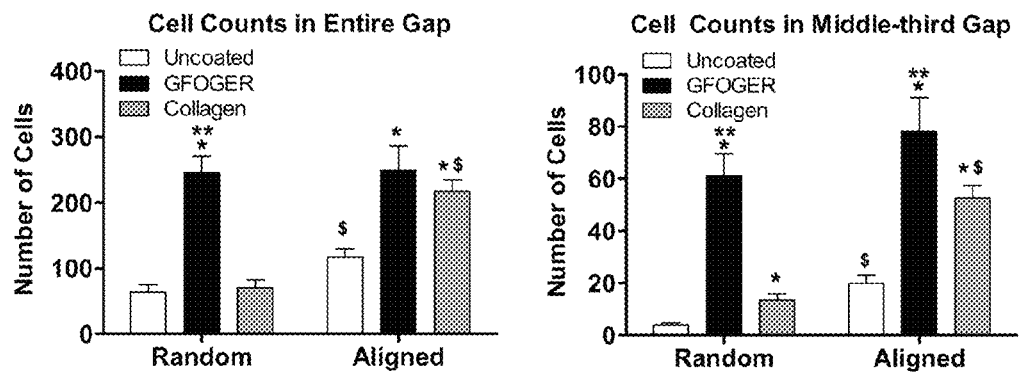
FIGURE 14
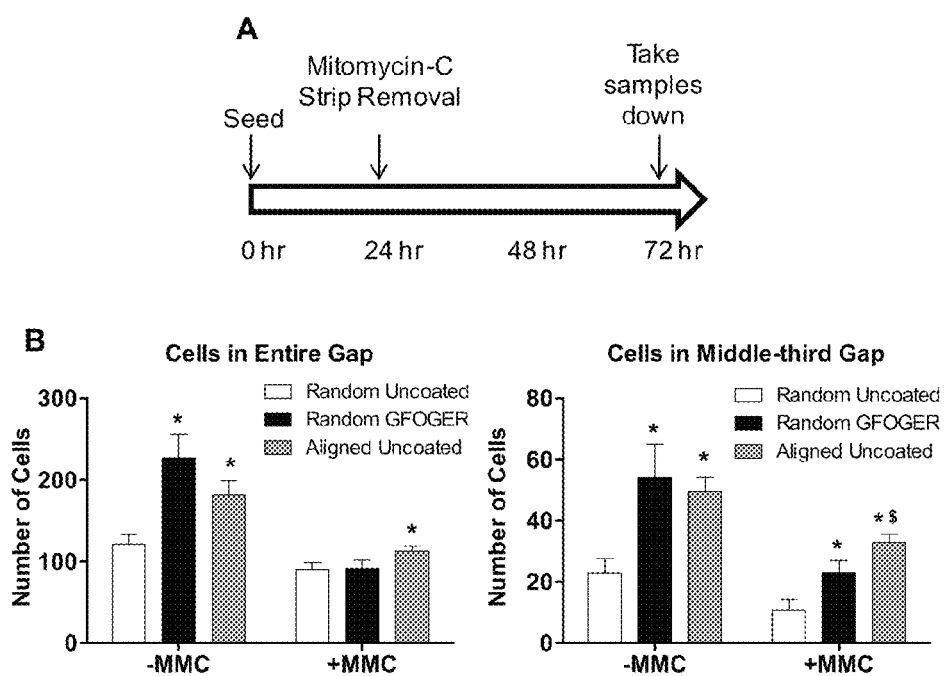
FIGURES 15A-B

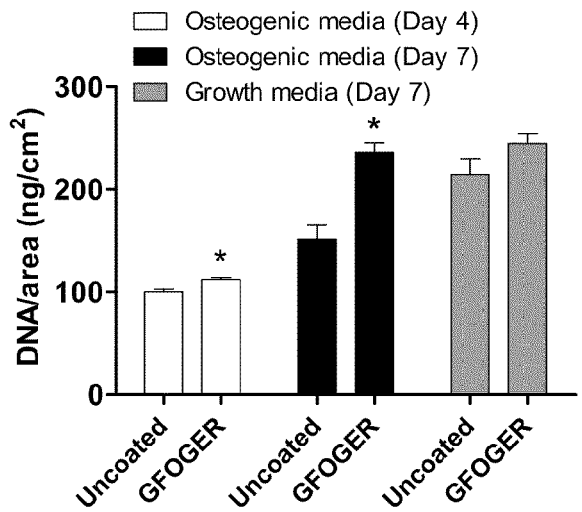
FIGURE 16
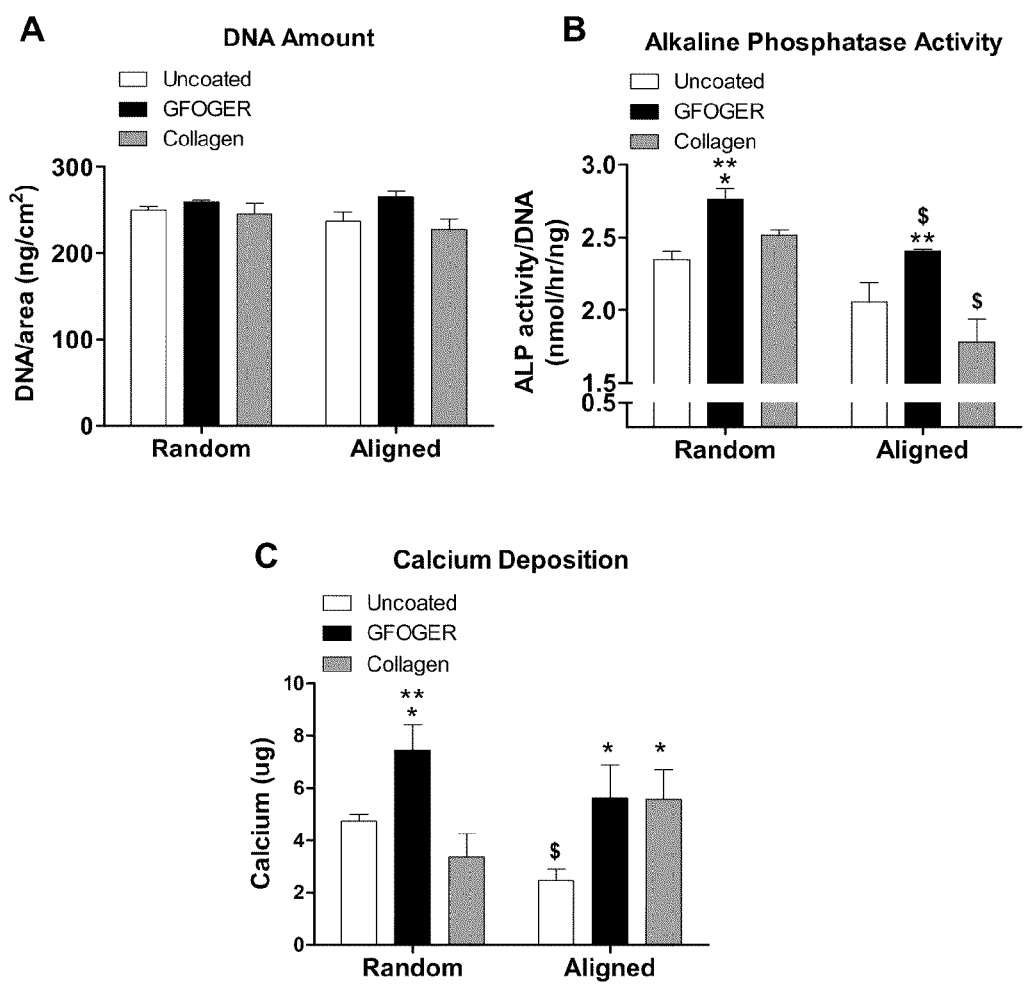
FIGURES 17A-C

FIGURES 19A-C

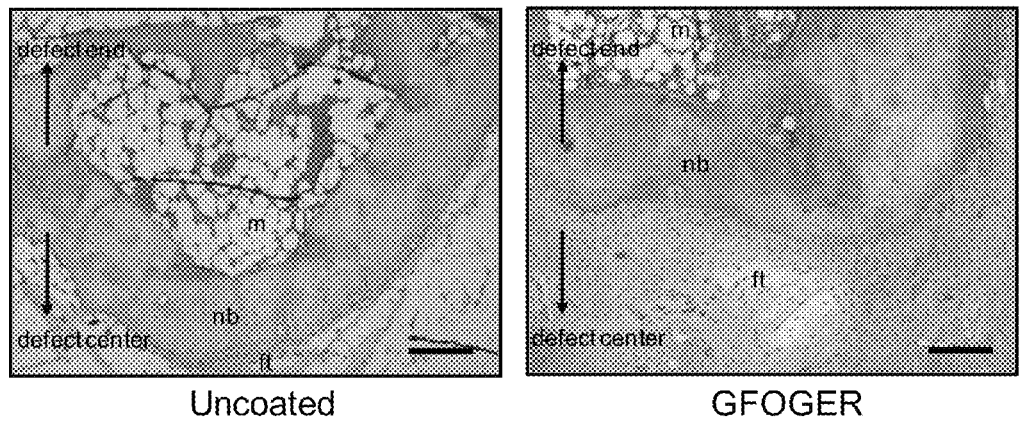
FIGURE 20
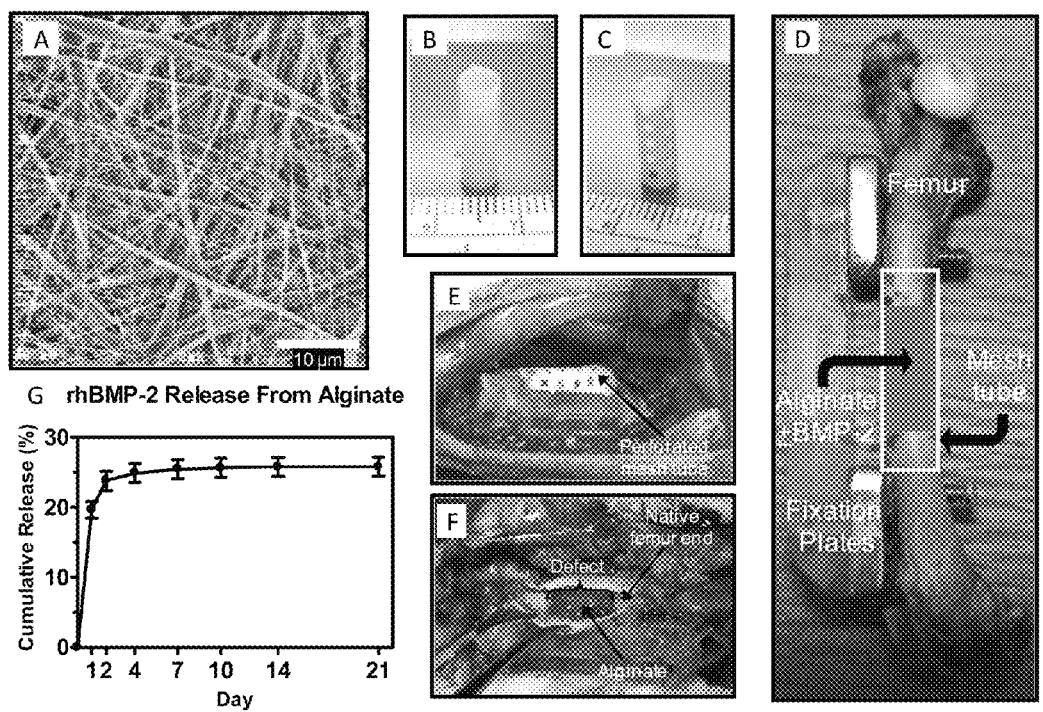
FIGURES 21A-G

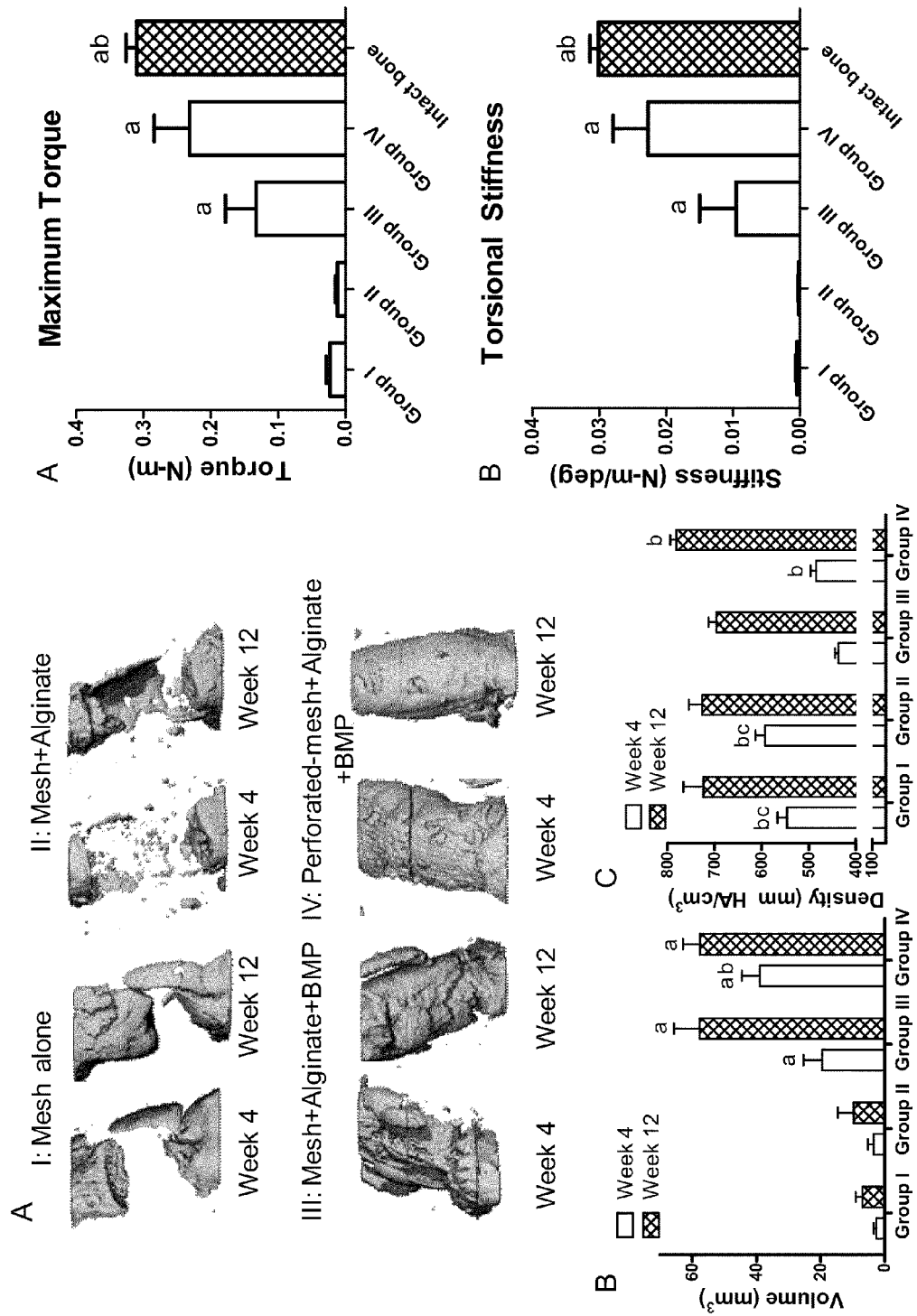
FIGURES 23A-C
FIGURES 24A-B

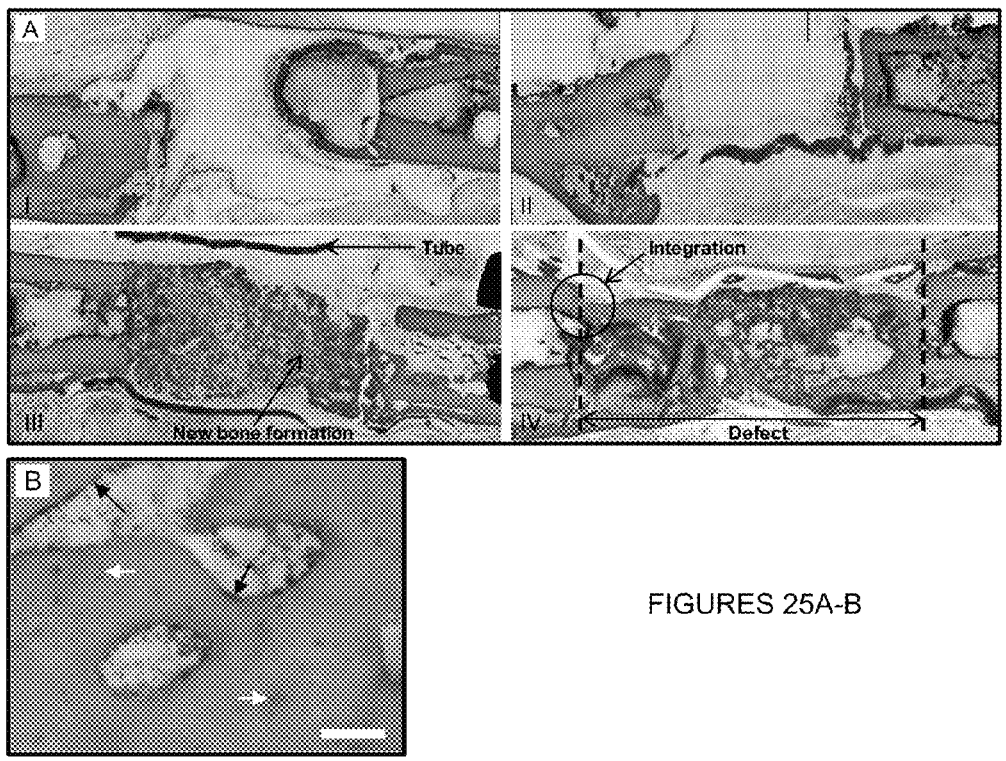
FIGURES 25A-B
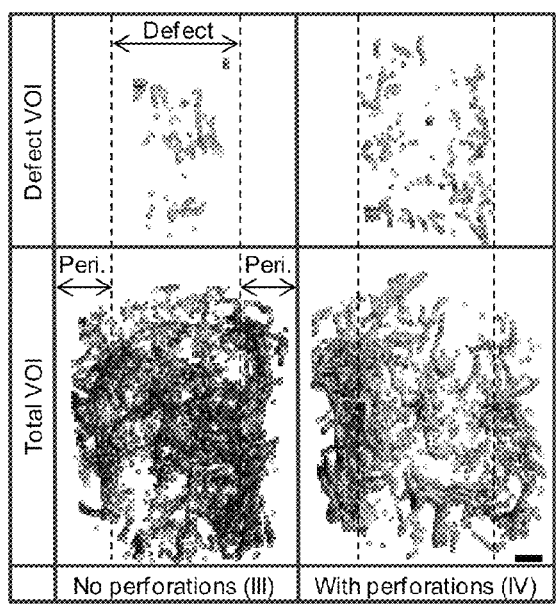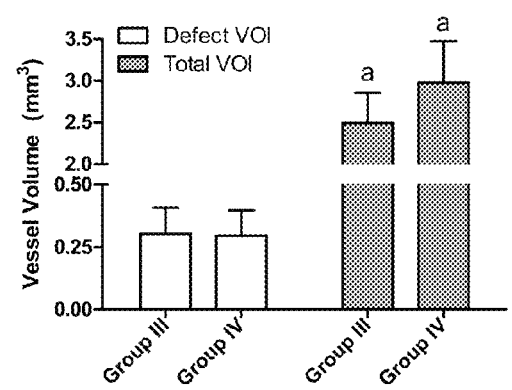
FIGURE 26

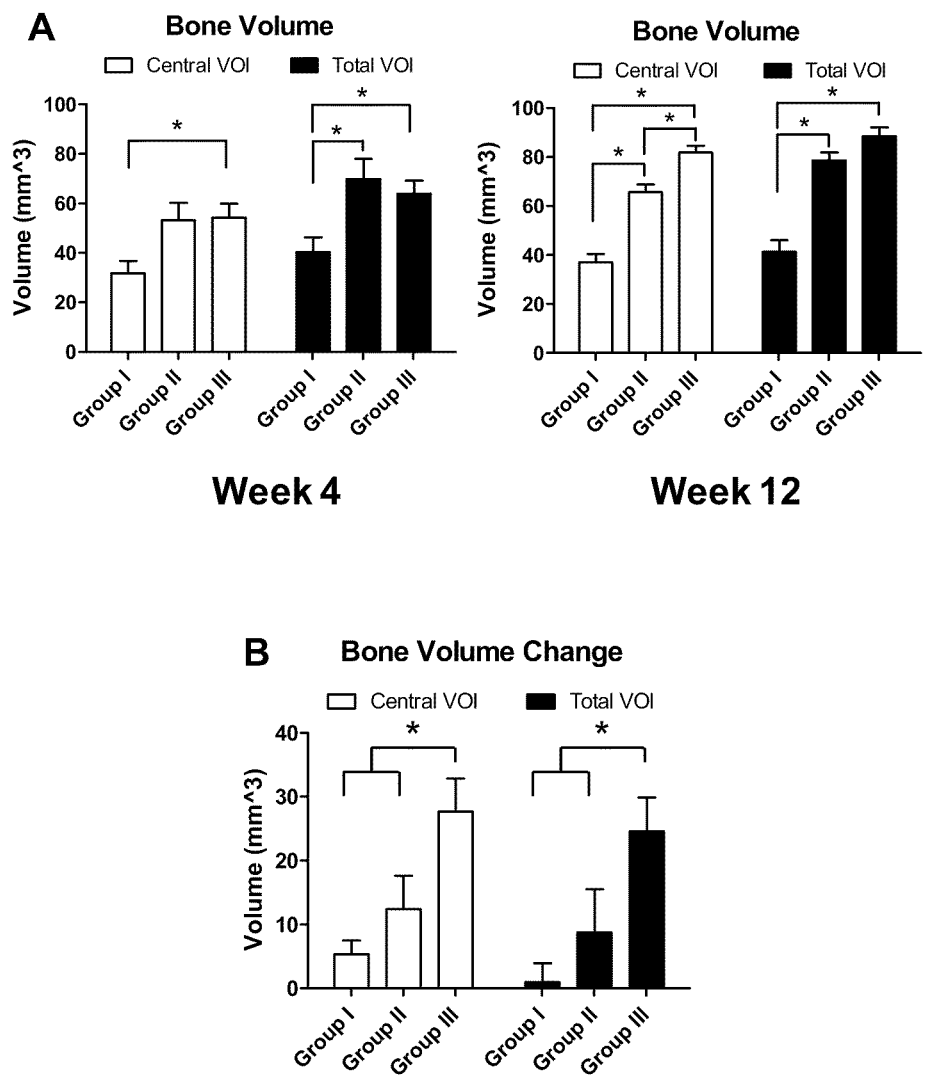
FIGURES 29A-B

FIGURES 30A-B

SYSTEMS AND METHODS TO AFFECT ANATOMICAL STRUCTURES

RELATED APPLICATION

This application claims, under 35 U.S.C. §119(e), the benefit of U.S. Provisional Application Ser. No. 61/117,399, filed 24 Nov. 2008, the entire contents and substance of which are hereby incorporated by reference as if fully set forth below.

STATEMENT REGARDING FEDERALLY SPONSORED RESEARCH

This invention was made with U.S. Government support under Grant No. EEC-9731643 awarded by the National Science Foundation, Grant No. 1 R01 AR051336-01 awarded by the National Institutes of Health, Grant No. W81XWH-08-1-0704 awarded to the Center for Advanced Bioengineering for Soldier Survivability through the Department of Defense. The U.S. Government has certain rights in the invention.

TECHNICAL FIELD OF THE INVENTION

The various embodiments of the present disclosure relate generally to systems and methods to affect anatomical structures. More particularly, the various embodiments of the present disclosure are related to systems and methods to regenerate bone.

BACKGROUND OF THE INVENTION

Approximately 2.2 million bone grafting procedures are performed worldwide to repair musculoskeletal defects, with approximately 500,000 bone grafting procedures being performed in the U.S. alone. Such musculoskeletal defects often result in pain and limited mobility, and therefore significantly impact the quality of life of affected individuals.

Bone is one of the few adult tissues with the capacity for true self-healing. Unlike soft tissue injuries, which generally result in the formation of scar tissue, bone healing concludes with the actual regeneration and reconstitution of the injured tissue, including the biochemical and biomechanical properties.

The need for bone regeneration arises in cases of bone loss due to trauma, tumor resection, or disease. Traditional orthopedic practice relies on the ability of a surgeon to drill, cut, ream, and realign bone. The success of these procedures requires technical skill and well-designed hardware. In a majority of cases, this is sufficient for healing, due largely to the remarkable capacity of bone for self-regeneration. Certain fractures and bone defects, however, require additional bone augmentation. The current procedures for bone augmentation include autologous and allogenic bone grafting, and more recently, ceramic and composite substitutes for bone grafts.

The clinical gold standard for bone regeneration has been autologous bone grafting, as it provides osteogenic cells and osteoinductive factors for bone healing. Though autologous bone grafting has been successful in many cases, it has significant disadvantages including limited graft material and morbidity of the donor site. These limitations have led to increased use of allograft bone as a substitute for autologous bone. Allograft bone, however, is inferior to autologous bone due to its reduced biological activity after processing.

In addition, allograft bone grafting is associated with a high rate of complications and late fractures as well as a risk of disease transmission. The high failure rate of allografts is largely attributable to the inability of the graft to revascularize and remodel. Ceramic and polymer based bone graft substitutes have recently been introduced and are being used frequently. But, ceramics tend to be brittle, and polymers suffer from limited bioactivity and strength and may need to be supplemented with osteogenic cells and growth factors.

Tissue engineering research has focused on therapeutic strategies for repairing bone defects by the delivery of biological agents along with biodegradable scaffolds. Both two- and three-dimensional scaffolds have been designed to provide a template for bone repair. Though the focus has been to create three-dimensional scaffolds having adequate strength to support in vivo loading, most scaffolds do not provide an optimal environment for cellular function, and suffer from slow resorption kinetics. Moreover, exogenous cells delivered at the center of these scaffolds in vivo may not survive due to the initial lack of vascularity at the defect. Thin, two-dimensional membranes have been used for bone repair by placing them along the periosteal surface to demarcate the osseous from the non-osseous region. Though this technique (called guided bone/tissue regeneration) has been highly successful in the dental field for bone regeneration, it has not been quantitatively evaluated for the load bearing case of long bone defects.

Accordingly, there is a need for improved bone grafting techniques that promote bone regeneration by facilitating cellular and vascular ingrowth into the defect space. It is to the provision of such improved systems and methods for regenerating bone that the various embodiments of the present invention are directed.

BRIEF SUMMARY OF THE INVENTION

The various embodiments of the present invention are directed to systems and methods to affect anatomical structures. More particularly, the various embodiments of the present invention are directed to systems and methods to regenerate bone. One aspect of the present invention includes a system for affecting an anatomical structure, comprising: a nanofiber mesh configured to substantially conform to an anatomical structure; and an active agent. In one embodiment, the system can further comprise a carrier substance, such as a hydrogel. According to such embodiments, at least a portion of the nanofiber mesh defines a fillable space, and the carrier substance can be disposed within the fillable space, to substantially fill the space. The nanofiber mesh can have an average pore size of less than about 100 micrometers, and the nanofiber mesh can further comprise a plurality of macropores.

In one embodiment of a system for affecting an anatomical structure, the active agent can comprise at least one member of the transforming growth factor-beta (TGF-β) superfamily, such as bone morphogenetic protein (BMP). In an exemplary embodiment of the present invention, the system for affecting an anatomical structure is used on a bone, and the carrier substance comprises alginate or a derivative thereof, the at least one member of the transforming growth factor-beta (TGF-β) superfamily comprises a bone morphogenetic protein (BMP). In another embodiment, the active agent can comprise a plurality of cells, such as mesenchymal progenitor cells.

Another aspect of the present invention includes a method for affecting an anatomical structure, comprising: adapting a nanofiber mesh to an anatomical structure of a subject so that the nanofiber mesh substantially conforms to the anatomical structure, wherein at least a portion of the nanofiber mesh defines a fillable space; and flowing a carrier substance into the fillable space, wherein the carrier substance comprises an active agent, and wherein at least a portion of the carrier substance is disposed within the fillable space. The nanofiber mesh can have an average pore size of less than about 100 micrometers.

The carrier substance can comprise a hydrogel, and the carrier substance can further comprise the active agent. In one embodiment, the active agent can comprise at least one member of the transforming growth factor-beta (TGF-β) superfamily. In an exemplary embodiment of the present invention, the anatomical structure comprises a bone, the carrier substance comprises alginate or a derivative thereof, and the at least one member of the transforming growth factor-beta (TGF-β) superfamily comprises a bone morphogenetic protein (BMP). In such embodiments, a method for affecting an anatomical structure can further comprise regenerating at least a portion of the bone of a subject, wherein the bone morphogenetic protein is present in an initial concentration of less than about 100 micrograms per kilogram of body weight of the subject. Methods for affecting an anatomical structure can also comprise using an active agent that comprises a plurality of mesenchymal progenitor cells.

Yet another aspect of the present invention includes a kit for affecting an anatomical structure, comprising: a membrane configured to substantially conform to an anatomical structure; and a flowable hydrogel system comprising at least one active agent. More specifically, the membrane can be a nanofiber mesh having an average pore size of less than about 100 micrometers, and the nanofiber mesh can further comprise a plurality of macropores. In an exemplary embodiment of the present invention, the kit is used to affect a bone, the flowable hydrogel comprises alginate or a derivative thereof, and the active agent comprises a bone morphogenetic protein, a plurality of mesenchymal progenitor cells, or combinations thereof.

Other aspects and features of embodiments of the present invention will become apparent to those of ordinary skill in the art, upon reviewing the following description of specific, exemplary embodiments of the present invention in conjunction with the accompanying figures.

BRIEF DESCRIPTION OF DRAWINGS

FIG. 1A is a representative scanning electron microscope (SEM) image of a nanofiber mesh at 10,000× magnification.

FIG. 1B is a histogram of nanofiber diameter of a representative nanofiber mesh.

FIG. 2A provides SEM images of random and aligned nanofiber meshes at 2000× magnification.

FIG. 2B graphically depicts fiber angle measurements of nanofiber meshes.

FIGS. 7A-C provide (A) a SEM image at low (1000×) magnification; (B) a SEM image at high (7000×) magnification; and (C) a nanofiber diameter histogram.

FIGS. 8A-D demonstrate sample cellularity through DNA quantity for cells cultured on (A) tissue culture plates and (B) nanofiber meshes. To compare the cellularity on nanofiber meshes with that on tissue culture plates, the data was plotted again for (C) hMSCs and (D) hAFS cells. (*—significantly different than the other cell type at same time point; #-significantly different than the previous time point for same cell type).

FIGS. 9A-B graphically depict the alkaline phosphatase activity of cell lysates on (A) tissues culture plates and (B) nanofiber meshes. (*—significantly different than the other cell type at same time point; #—significantly different than a previous time point for same cell type; $—significantly different than hMSC peak on plate at day 7).

FIG. 10 graphically depicts calcium quantification deposited by cells. (#—significantly different than growth media; *—significantly different than other cell type on same surface; $—significantly different than plate with same cell type).

FIG. 11 graphically depicts calcein staining quantified by fluorescence (*—significantly greater than MSC osteogenic media; #—significantly greater than growth media with same cell type).

FIGS. 13A-B illustrate the kinetics of cell infiltration on uncoated random nanofiber meshes. (* indicates significantly greater than cell number on day 0. # indicates significantly greater than cell number on days 3 and 4. Significance was set at p<0.05).

FIG. 14 graphically depicts the effect of coating and fiber alignment on cell infiltration at 48 hours after strip removal. (** indicates significantly greater than collagen with same fiber orientation. $ indicates greater than random orientation with same coating. Significance was set at p<0.05).

FIGS. 15A-B demonstrate the role of cell proliferation in the cell infiltration model. (* indicates significantly greater than random uncoated with same MMC condition (p<0.05). $ indicates significantly greater than random GFOGER with same MMC condition (p<0.05)).

FIG. 16 graphically depicts the early effect of GFOGER coating on hMSC number. (* indicates significantly greater than uncoated in the same group).

FIGS. 17A-C demonstrate the effect of coating and fiber alignment on cell number and osteogenic differentiation of hMSCs in osteogenic media through (A) DNA amount, (B) alkaline phosphatase (ALP) activity, and (C) calcium deposition.

FIG. 19A illustrates regenerated bone volume from μCT analysis FIG. 19B demonstrates failure strength derived from the maximum torque in torsional testing.

FIG. 19C illustrates cross sections of μCT images of regenerated bone.

FIG. 20 shows histological analysis of newly formed bone with hematoxylin and eosin staining at 12 weeks. The defect in both groups contains a combination of newly formed bone (nb), fibrous tissue (ft) and marrow (m). Scale bars are 200 μm.

FIG. 21A is a SEM image of an electrospun nanofiber mesh.

FIG. 21B illustrates a hollow tubular implant without perforations made from nanofiber meshes.

FIG. 21C illustrates hollow tubular implant with perforations made from nanofiber meshes.

FIG. 21D illustrates implants in segmental bone defect.

FIG. 21E displays a photograph of the defect in a subject following placement of a perforated mesh tube.

FIG. 21F displays a photograph of the defect in a subject after a one week incubation with the nanofiber mesh tube.

FIG. 21G graphically depicts alginate release kinetics over 21 days in vitro.

FIG. 23A illustrates μCT images of bone regeneration at 4 and 12 weeks.

FIG. 23B graphically depicts quantification of regenerated bone volume.

FIG. 23C graphically depicts mean density of regenerated bone.

FIGS. 24A-B demonstrate the mechanical properties, (A) maximum torque and (B) torsional stiffness, of femora at 12 weeks.

FIGS. 25A-B provide a histological analysis at 12 weeks (A) 4× magnification, (B) 10× magnification. White arrows point to osteocytes embedded in lacunae. Black arrows point to osteoblasts lining the bone surface. Scale bar is 100 μm.

FIG. 26 illustrates vascular ingrowth at a defect site at 3 weeks. Scale bar is 1 mm and applies to all images. "Peri" refers to periphery of defect.

FIGS. 29A-B demonstrate quantitative μCT analysis of new bone volume. (* indicates significantly different ($p<0.05$)).

FIGS. 30A-B demonstrate mean density (A) and connectivity density (B) of the newly formed bone, obtained from μCT analysis. (* indicates significantly different ($p<0.05$)).

DETAILED DESCRIPTION OF THE INVENTION

Figure 3:
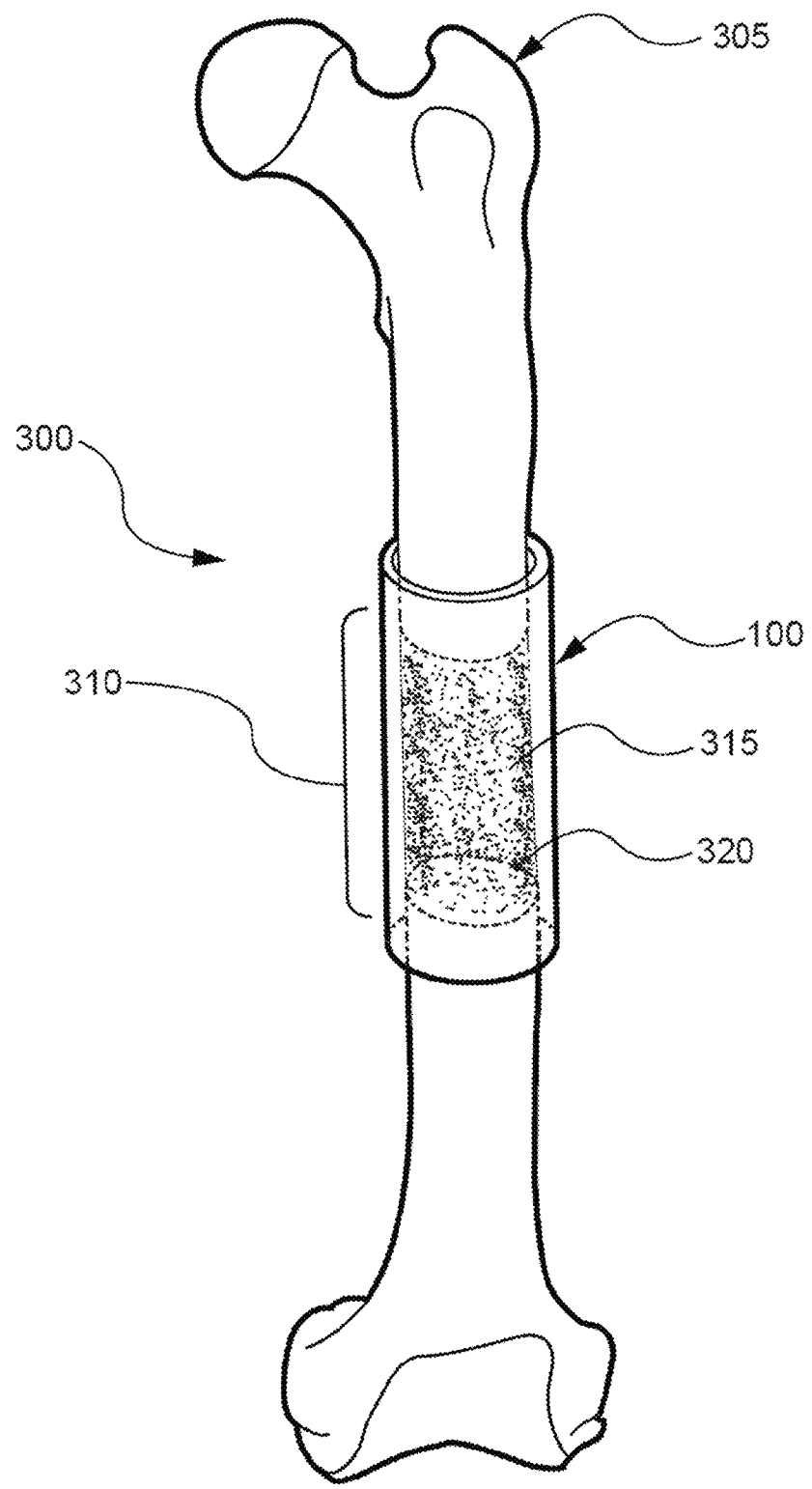
FIG. 3 is a perspective view of one embodiment of a system for affecting an anatomical structure, such as a long bone.

Referring now to the figures, wherein like reference numerals represent like parts throughout the several views, exemplary embodiments of the present invention will be described in detail. Throughout this description, various components can be identified as having specific values or parameters, however, these items are provided as exemplary embodiments. Indeed, the exemplary embodiments do not limit the various aspects and concepts of the present invention as many comparable parameters, sizes, ranges, and/or values can be implemented. The terms "first," "second," and the like, "primary," "secondary," and the like, do not denote any order, quantity, or importance, but rather are used to distinguish one element from another. Further, the terms "a," "an," and "the" do not denote a limitation of quantity, but rather denote the presence of "at least one" of the referenced item.

The various embodiments of the present invention provide systems and methods to affect anatomical structures of a subject. As used herein, the term "subject" refers to animals and plants, as well as cells and tissues derived therefrom. For example, the systems and methods of the present invention are applicable to a broad range of vertebrate animals, preferably mammals, and more preferably humans. Mammals include, but are not limited to, humans, primates, horses, cows, sheep, pigs, goats, dogs, cats, rabbits, guinea pigs, rats, and mice.

As used herein, the term "anatomical structure" can refer to many anatomical structures of animals or plants. Accordingly, an anatomical structure of an animal can include, but is not limited to, bone, cartilage, tendons, ligaments, muscle, tumors, nerve, skin, organs, and tissues. In an exemplary embodiment of the present invention, an anatomical structure is bone, such as short bones, flat bones, and long bones. The term "anatomical structure" also encompasses defects, injuries, trauma, lesions, and the like that are associated with an anatomical structure.

As used herein, the phrase "to affect an anatomical structure" refers to acting on or producing an effect or a change in the structure or function of an anatomical structure. Therefore, "to affect an anatomical structure" refers to a difference in degree from a first state, such as an untreated state in a subject, to a second state, such as a treated state in a subject. Consequently, the various embodiments of the systems and methods of the present invention can function to alter one or more various anatomical, physiological, and pathological properties of an anatomical structure. The alteration of one or more various anatomical, physiological, and pathological properties of an anatomical structure can include, but are not limited to, promoting or inhibiting cellular infiltration, promoting or inhibiting cellular proliferation, promoting or inhibiting cellular differentiation, promoting or inhibiting cellular survival, promoting or inhibiting angiogenesis, promoting or inhibiting an immune response, or promoting or inhibiting matrix synthesis or organization, among others. The alteration of one or more anatomical property, physiological property, pathological property, or various combinations thereof will depend upon the desired therapeutic effect. For example, in the context of a long bone defect resulting from a trauma, alteration of one or more anatomical, physiological, or pathological properties can include promotion of cellular proliferation, infiltration, and differentiation as well as promotion of angiogenesis in the defect site. Alternatively, in the context of craniosynostosis, alteration of one or more anatomical, physiological, or pathological properties can include inhibition of cellular proliferation, infiltration, and differentiation or inhibition of angiogenesis into the defect site. In yet another example, in the context of a malignant tumor, alteration of one or more anatomical, physiological, or pathological properties can include inhibition of cellular proliferation or survival, inhibition of angiogenesis, or stimulation of an immune response.

In one embodiment of the present invention, a system for affecting an anatomical structure comprises: a nanofiber mesh configured to substantially conform to an anatomical structure or defect region; and an active agent. A nanofiber mesh 100 can comprise a plurality of nanofibers 105, as shown in FIG. 1. As used herein, the term "plurality" means more than one. The nanofiber mesh 100 is a porous, substantially flattened structure composed of a plurality of interconnected nanofibers 105, as shown in FIG. 1A. In another embodiment of the present invention, the nanofiber mesh 100 is plurality of interconnected microfibers (i.e., fibers having an average longest cross-sectional dimension greater than about 1000 nm). In yet another embodiment of the present invention, the nanofiber mesh 100 can comprise a one or more of nanofibers and one or more macrofibers.

A nanofiber 105 comprises many classes of materials that are continuous, flexible, filaments or are in discrete elongated pieces, similar to lengths of thread. As used herein, a "nanofiber" means a continuous, flexible, filamentous material having a relatively high aspect ratio (i.e., ratio of length to average longest cross-section). In an embodiment of the present invention, an aspect ratio can be at least about 5:1. In an embodiment of the present invention, an aspect ratio can be at least about 10:1, at least about 100:1, or at least about 1000:1.

A nanofiber 105 can have many cross-sectional shapes, including, but not limited to, a rectangular shape, a circular shape, a semicircular shape, a square shape, a pentagonal shape, a triangular shape, a hexagonal shape, an octagonal shape, a star-shape, a starburst shape, a "U" shape, a lobed shape, a multi-lobed shape, an arbitrary shape, or combinations thereof or therebetween. In an exemplary embodiment of the present invention, a nanofiber 105 has a circular cross-sectional shape; however, one of ordinary skill in the art would realize that the cross-sectional shape of the nanofiber 105 can be varied to impart additional properties to the nanofiber 105 or nanofiber mesh 100, such as increased surface area.

One of ordinary skill in the art would also realize that the cross-sectional shape of the nanofiber 105 will determine the average longest cross-sectional dimension of the nanofiber 105. For example, the average longest cross-sectional dimension of a nanofiber 105 having a circular cross-sectional shape will be the diameter of the nanofiber 105. In an alternative example, the average longest cross-sectional dimension of a nanofiber 105 having a rectangular cross-sectional shape will be the length (with the proviso that the so-called length is greater than the so-called width) of the rectangular cross-section of the nanofiber 105. In yet another example, the average longest cross-sectional dimension of a nanofiber 105 having a starburst cross-sectional shape will be the distance between the two furthest points of the starburst cross-section of the nanofiber 105.

In an embodiment of the present invention, a nanofiber 105 has an average longest cross-sectional dimension ranging from about 10 nm to about 1000 nm. In another embodiment of the present invention, a nanofiber 105 has an average longest cross-sectional dimension ranging from about 50 nm to about 600 nm. In yet another embodiment of the present invention, a nanofiber 105 has an average longest cross-sectional dimension ranging from about 50 nm to about 300 nm. In yet another embodiment of the present invention, a nanofiber 105 has an average longest cross-sectional dimension ranging from about 50 nm to about 300 nm (FIG. 1B). In still another embodiment of the present invention, a nanofiber 105 has an average longest cross-sectional dimension ranging from about 50 nm to about 150 nm. In an exemplary embodiment of the present invention, a nanofiber 105 has an average longest cross-sectional dimension of about 150 nm.

The nanofibers 105 of the present invention can be made of many biocompatible materials, including degradable materials, non-degradable materials, or combinations thereof. Examples of such materials include but are not limited to, polytetrafluoroethylenes, perfluorinated polymers, polypropylenes (e.g., polypropylene fumarate), polyethylenes (e.g., polyethylene glycol), polyethylene terapthalates, silicones, silicone rubber, polysulfones, polyurethanes, polycarboxylates, polycarbonates, polyketals, polyesters (e.g., polylactic acid and polyglycolic acid), polyorthoesters, polyacrylics, polyhydroxymethacrylates, polymethylmethacrylates, polyamides, polycaprolactones, polyanhydrides, collagen, agarose, alginate, gelatin, fibrinogen, silk, chitosan, hyaluronic acid, co-polymers thereof, and combinations thereof. In one exemplary embodiment of the present invention, the nanofibers 105 are made of poly ($\epsilon$-caprolactone). In an exemplary embodiment of the present invention, the nanofibers 105 are made of poly (L, DL lactide).

According to one embodiment of the present inventions, the nanofiber mesh 100 is produced by electrospinning Electrospinning has recently emerged as a technique to produce polymeric scaffolds for tissue engineering, with fiber diameters ranging from tens of nanometers to as large as 10 micrometers. The nanofiber mesh obtained by this process is a unique scaffold membrane that possesses structural features with a size scale similar to extracellular matrix (ECM) components, high porosity and large surface area to volume ratios. These properties allow for enhanced cellular attachment and spreading. Therefore, nanofiber meshes serve as an effective delivery vehicle for cells to a defect site in vivo.

The nanofiber mesh 100 may have a network of randomly-oriented nanofibers 105 or may have a network of substantially aligned nanofibers 105, as shown in FIGS. 2A-B. A substantially aligned nanofiber mesh 100 has a majority of nanofibers 105 oriented in the same direction. Stated another way, a substantially aligned nanofiber mesh 100 comprises a plurality of nanofibers 105, where more than about 85% of the nanofibers are aligned substantially parallel to an arbitrary line (i.e., within −45° and +45° of the arbitrary line). Conversely, a randomly-oriented nanofiber mesh 100 comprises a plurality of nanofibers 105, where less than about 85% of the nanofibers are aligned substantially parallel to an arbitrary line. In an exemplary embodiment of the present invention, a randomly-oriented nanofiber mesh 100 comprises a plurality of nanofibers 105, where less than about 55% of the nanofibers are aligned substantially parallel to an arbitrary line.

The nanofiber mesh 100 is a porous, substantially flattened structure composed of a plurality of interconnected nanofibers 105, as shown in FIG. 1A. The nanofiber mesh 100 can have an average thickness ranging from about 50 nm to about 10 mm. In an exemplary embodiment of the present invention, the nanofiber mesh 100 has an average thickness ranging from about 100 nm to about 1 mm. In another exemplary embodiment, the nanofiber mesh 100 has an average thickness ranging from about 300 µm to about 400 µm.

The plurality of interconnected nanofibers 105 creates a network or mesh of fibers, which confers the nanofiber mesh 100 with plurality of pores 110 (FIG. 1A). These pores 110 may have varying characteristics, such as size, shape, and tortuosity. Preferably, the pores 110 are constructed such that they pass directly through the nanofiber mesh 100. In one embodiment of the present invention, the pores 110 have an average longest cross-sectional dimension of less than about 100 µm. In another embodiment of the present invention, the pores 110 have an average longest cross-sectional dimension of less than about 10 µm. In another embodiment of the present invention, the pores 110 have an average longest cross-sectional dimension of less than about 5 µm. In yet another embodiment of the present invention, the pores 110 have an average longest cross-sectional dimension of less than about 2 µm. In yet another embodiment of the present invention, the pores 110 have an average longest cross-sectional dimension of about 1 µm.

The nanofiber mesh 100 is a substantially flattened structure, composed of a network of biocompatible nanofibers 105, that can be configured to substantially conform to an anatomical structure. Configuring the nanofiber mesh 100 to substantially conform to an anatomical structure may take place during construction of the mesh. Alternatively, the nanofiber mesh 100 may be configured after construction, for example during implantation. In yet another alternative, the nanofiber mesh 100 may be configured during construction and further configured after construction.

When implanted, the nanofiber mesh 100 can be configured to define a fillable space. Therefore, the implanted nanofiber mesh 100 provides a porous permeable membrane between the established fillable space of the anatomical structure and the milieu surrounding the anatomical structure. As used herein, the phrase "substantially conform to an anatomical structure" refers to situations where the nanofiber mesh 100 may delineate the entire boundary of the space, or alternatively, the nanofiber mesh 100 may delineate only a portion of the space and the remainder of the boundary being delineated by the anatomical structure or adjacent structures or tissues of the subject. The parameters and configuration of the fillable space established by implantation of the nanofiber mesh 100 is approximately equivalent to the anatomical structure or defect associated therewith that is desired for treatment with the systems and methods of the present invention.

FIG. 3 illustrates one example of a system 300 for affecting an anatomical structure, such as bone 305. The system comprises a nanofiber mesh 100 is configured to substantially conform to an anatomical structure, in this case a long bone 305. The nanofiber mesh 100 is configured to define a fillable space 310. In this case, the nanofiber mesh 100 is wrapped around the bone defect to establish a fillable space 310 for bone growth.

Various embodiments of the systems and methods for affecting an anatomical structure include an active agent 320. As used herein, the term "active agent" can include, without limitation, agents for gene therapy, analgesics, anti-arthritics, anti-asthmatic agents, anti-cholinergics, anti-convulsants, anti-depressants, anti-diabetic agents, anti-diarrheals, anesthetics, antibiotics, antigens, anti-histamines, anti-infectives, anti-inflammatory agents, antimicrobial agents, anti-migraine preparations, anti-nauseants, anti-neoplastics, anti-parkinsonism drugs, anti-pruritics, anti-psychotics, anti-pyretics, anti-spasmodics, anorexics, anti-helminthics, antiviral agents, nucleic acids, DNA, RNA, polynucleotides, nucleosides, nucleotides, amino acids, peptides, proteins, carbohydrates, lectins, lipids, fats, fatty acids, viruses, antigens, immunogens, antibodies and fragments thereof, sera, cytokines, chemokines, immune stimulants, immune suppressors, sympathomimetics, xanthine derivatives, cardiovascular agents, potassium channel blockers, calcium channel blockers, beta-blockers, alpha-blockers, anti-arrhythmics, anti-hypertensives, diuretics, anti-diuretics, vasodilators comprising general, coronary, peripheral, or cerebral, central nervous system stimulants, vasoconstrictors, gases, growth factors, growth inhibitors, hormones, estradiol, steroids, progesterone and derivatives thereof, testosterone and derivatives thereof, corticosteroids, angiogenic agents, anti-angiogenic agents, hypnotics, muscle relaxants, parasympatholytics, psychostimulants, sedatives, tranquilizers, ionized and non-ionized active agents, antifungal agents, metals, small molecules, pharmaceuticals, hemotherapeutic agents, wound healing agents, indicators of change in the bio-environment, enzymes, nutrients, vitamins, minerals, coagulation factors, neurochemicals, cellular receptors, radioactive materials, cells, chemical or biological materials or compounds that induce a desired biological or pharmacological effect, and combinations thereof.

In an exemplary embodiment of the present invention, the active agent 320 comprises at least one member of the transforming growth factor-beta (TGF-β) superfamily. Members of the TGF-β superfamily, include but are not limited to, TGF-β (e.g., TGF-β1, TGF-β2, TGF-β3) bone morphogenetic protein (BMP) (e.g., BMP2, BMP3, BMP4, BMP5, BMP6, BMP7, BMP8a, BMP8b, BMP10, BMP11, BMP12, BMP13, BMP14, BMP15), inhibin (e.g., Inhibin A, Inhibin B), activin (e.g., Activin A, Activin B, Activin AB), growth differentiation factor (GDF1, GDF2, GDF3, GDF3A, GDF5, GDF6, GDF7, GDF8, GDF9, GDF10, GDF11, GDF15), Nodal, Lefty (e.g., Lefty 1, Lefty2), and anti-Müllerian hormone (sometimes referred to as Müllerian Inhibiting Substance), among others. More specifically, the active agent can be recombinant human BMP2 (rhBMP2) or recombinant human BMP7 (rhBMP7), or combinations thereof. In another exemplary embodiment of the present invention, the active agent 320 may comprise a growth factor, such as insulin-like growth factor 1 (IGF-1), vascular endothelial growth factor (VEGF), platelet-derived growth factor (PDGF), or fibroblast growth factor (FGF).

In another exemplary embodiment, the active agent 320 can comprise a cell or a plurality of cells, such as a mesenchymal progenitor cell, which can be derived from amniotic fluid, bone marrow, adipose tissue, and the like. Bone marrow derived mesenchymal stem cells (MSCs) have demonstrated a strong potential for differentiation into bone forming cells and have been shown to promote repair of critically-sized bone defects in pre-clinical animal studies. Other cells that may be suitable for applications related to regeneration and remodeling of bone include, but are not limited to, osteoblasts, osteoclasts, osteocytes, and bone-lining cells In one embodiment of the present invention, the nanofiber mesh 100 can be functionalized or surface-modified with one or more active agents. For example, the nanofiber mesh 100 can be functionalized or surface-modified with an osteogenic biomolecule. As used herein, the term "biomolecule" refers many organic molecules that are produced by a living organism, including large polymeric molecules such as proteins, polysaccharides, and polynucleotides, including smaller peptides, oligosaccharides, and nucleic acids, as well as small molecules such as primary metabolites, secondary metabolites, and other biological products. In one exemplary embodiment, the nanofiber mesh can be functionalized or surface-modified to mimic the extracellular matrix. For example, the osteogenic biomolecule can include proteoglycans, proteins, peptides, polysaccharides, and components thereof, among others. As used herein, "mimicking the extracellular matrix" refers to biomolecules (e.g., proteoglycans, proteins, peptides, polysaccharides, and components thereof) having structural identity to a component of the extracellular matrix or sufficient structural homology to a component of the extracellular matrix, thereby effectively replicating the same interactions associated with that component of the extracellular matrix. These biomolecules can include, but are not limited to, glycosaminoglycans (e.g., chondroitin sulfate, heparin sulfate, keratin sulfate, hyaluronic acid), or proteins (e.g., collagen, elastin, fibronectin, laminin) or peptides derived from these proteins (e.g., glycine-phenylalanine-hydroxyproline-glycine-glutamate-arginine (GFOGER) domain from residues 502-507 of the $\alpha_1(I)$ chain of type I collagen), among others.

The system for affecting an anatomical structure can further comprise a carrier substance 315. As used herein, the term "carrier substance" can comprise many media, including but not limited to, a fluid, liquid, solid, solution, suspension, emulsion, gas, vapor, gel, dispersion, a flowable material, a multiphase material, or combination thereof. In an exemplary embodiment of the present invention, the carrier substance comprises a flowable polymer. The flowable polymer can comprise many suitable hydrophilic, hydrophobic, and amphiphilic polymers known in the art. In some embodiments of the present invention, the flowable polymer can comprise a hydrophilic polymer, including, but not limited to, acrylates, acrylamides, acetates, acrylic acids, vinyl alcohols, glycols, polysaccharides, co-polymers thereof, or combinations thereof. In various embodiments of the present invention, the polymer can have many topologies including, but not limited to, a branched topology, a graft topology, a comb topology, a star topology, a cyclic topology, a network topology, or combinations thereof, among others. The crosslinker of the polymer particles can be many suitable crosslinkers known in the art including, but not limited to, N,N', methylenebis(acrylamide), poly(ethylene glycol) (PEG) diacrylate, N,N'-dihydroxyethylene-bisacrylamide, N,O-(dimethacryloyl)hydroxylamine, ethylene glycol dimethacrylate, divinylbenzene, divalent cations (e.g., $Ca^{2+}$ and $Mg^{2+}$), or combinations thereof. In an exemplary embodiment of the present invention, the carrier substance comprises an alginate or a derivative thereof. Such derivatives are described in U.S. Pat. No. 6,642,363, which is incorporated by reference in its entirety. An example of an alginate derivative is alginate modified with a $G_4RGDASSP$ peptide sequence.

Accordingly, an embodiment of the present invention comprises a method for affecting an anatomical structure, which involves adapting a nanofiber mesh 100 to an anatomical structure of a subject so that the nanofiber mesh substantially conforms to the anatomical structure, and at least a portion of the nanofiber mesh 100 defines a fillable space 310 followed by flowing a carrier substance 315 into the fillable space 310. Thus, the flowable carrier substance 315 is capable of substantially filling the fillable space 310. In the context of regeneration of bone in a bone defect, the flowable aspect of the carrier substance provides a significant advancement over prior art methods, which utilize pre-formed gels. According to the systems and methods of the present invention, a flowable carrier substance 315 (e.g., an injectable hydrogel system) permits complete or near complete filling of the space 310 created by the nanofiber mesh 100. As shown in FIG. 3, the fillable space 310 can be filled with a carrier substance 315, such as a hydrogel, comprising an active agent 320. Thus, the use of a flowable hydrogel system may be readily adapted for use in not only nanofiber meshes, microfiber meshes, and combinations thereof, but can also be used with membranes (i.e., polymer films, which can be made of many the degradable materials, non-degradable materials, or combinations thereof, described above).

In one exemplary embodiment of the present invention, the carrier substance 315 can contain the active agent 320. In an exemplary embodiment of the present invention, the carrier substance comprises alginate or a derivative thereof, and the active agent comprises a member of the TGF-β superfamily, such as a bone morphogenetic protein (BMP).

Figure 4:
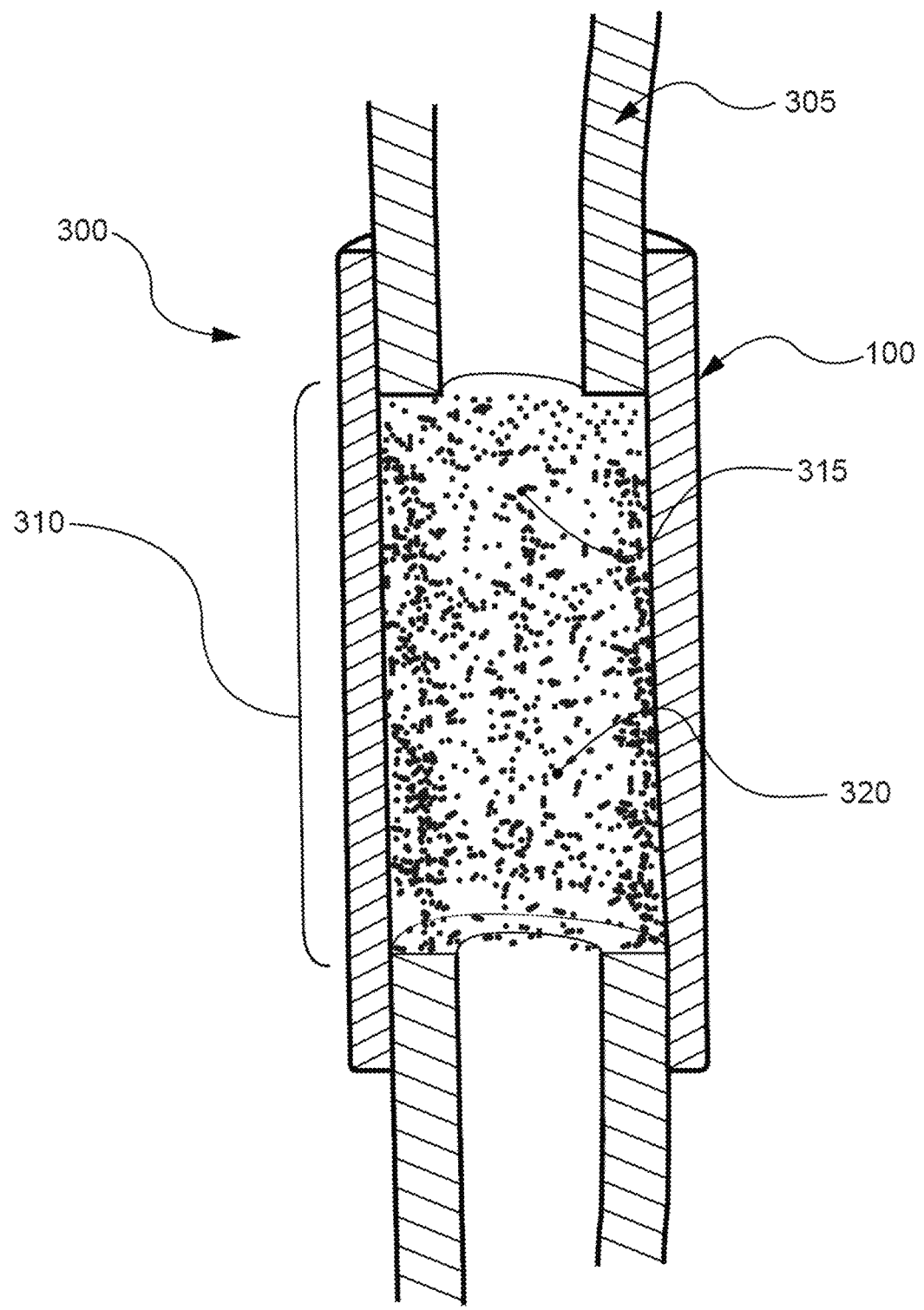
FIG. 4 is a cross section of one embodiment of a system for affecting an anatomical structure, such as a long bone.

Although not wishing to be bound by any particular theory, it is believed that the nanofiber mesh and flowable hydrogel carrier operate synergistically to promote new bone growth. In methods for repairing a bone defect, the nanofiber mesh 100 is positioned on the periosteal surface to define a space 310, as shown in FIG. 4. The flowable hydrogel carrier 315, which contains the active agent 320, operates to effectively fill the defect space 310 defined by the at least a portion of the nanofiber mesh 100 and the bone 305. Upon polymerization, the polymerized hydrogel 315 retains the active agent 320 at the defect site, which permits sustained delivery of the active agent 320, thereby promoting the infiltration and proliferation of osteoprogenitor cells. The nanofiber mesh 100, in turn, provides a substrate to facilitate the migration and proliferation of progenitor cells on the periosteal surface. The porosity of the nanofiber mesh 100 permits sufficient retention of the active agent 320 at the defect site, while allowing for the release of the active agent 320 (through diffusion or hydrogel degradation), which establishes a gradient to attract osteoprogenitor cells to the defect site. In addition, it is believed that the porosity of the nanofiber mesh 100 permits the infiltration of nutrients to the defect site.

In various embodiments of the present invention, the nanofiber mesh can be attached to the anatomical structure with the use of various biocompatible fastening elements, such as sutures, staples, tacks, screws, adhesives, or other fastening elements known in the art of fixing articles to anatomical structures. Alternatively, the nanofiber mesh may simply be surgically placed on the anatomical structure without using an attachment element.

Figure 5:
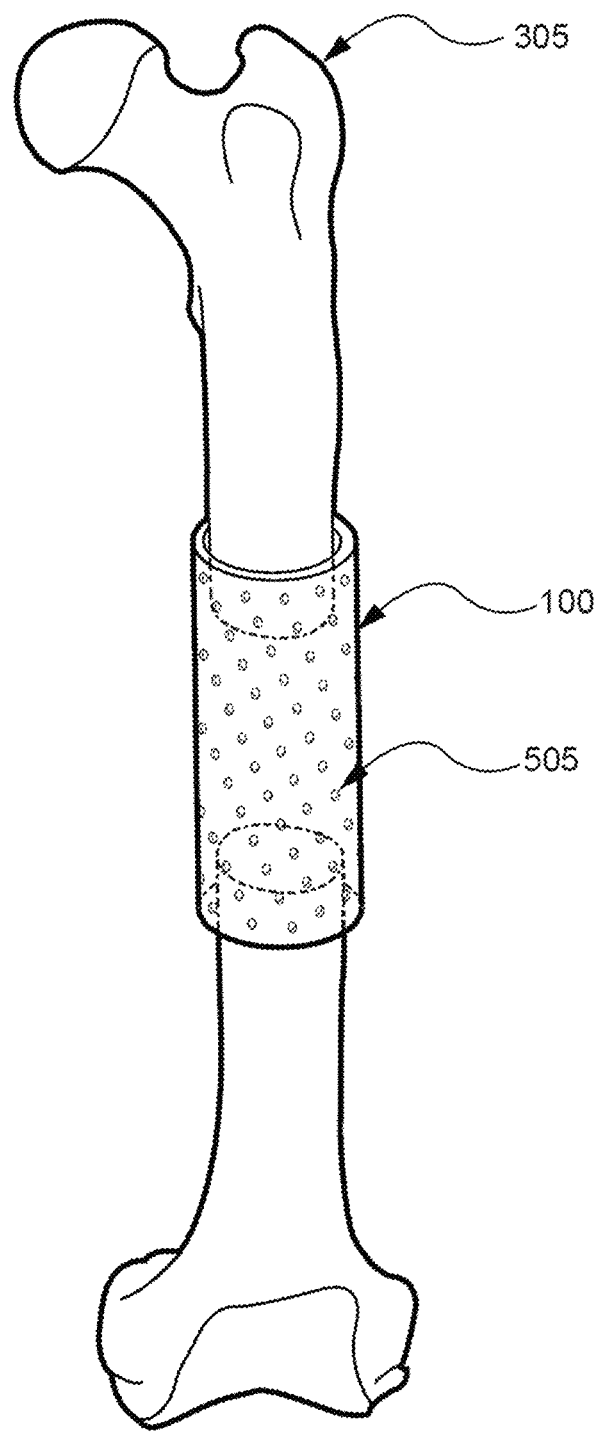
FIG. 5 is a perspective view of one embodiment of a system for affecting an anatomical structure having macropores.
Figure 6:
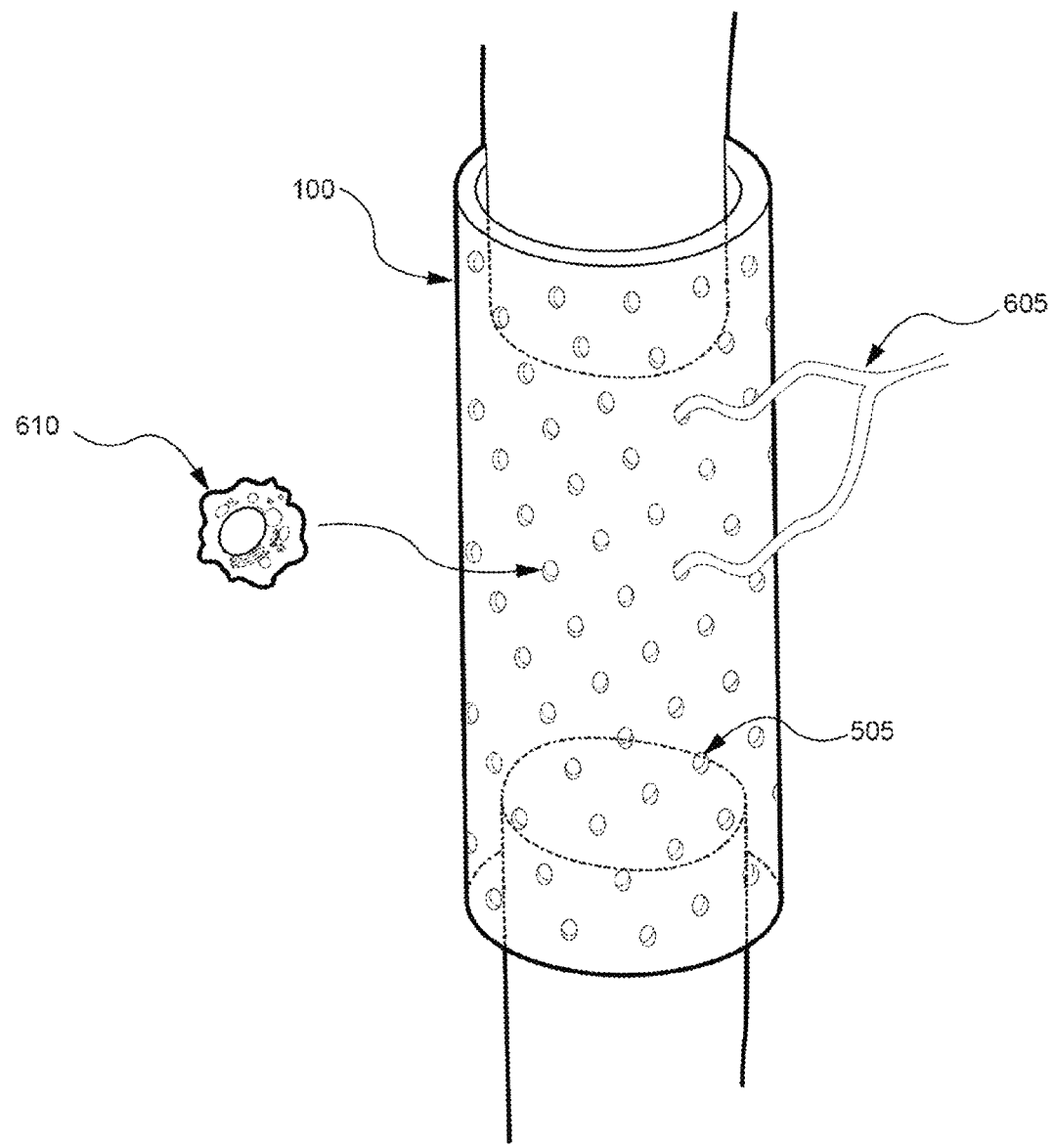
FIG. 6 illustrates the infiltration of cells and angiogenesis promoted by one embodiment of a system for affecting an anatomical structure having macropores.

In an attempt to further facilitate the infiltration of cells osteoprogenitor cells and the invasion of vasculature to the defect site, the nanofiber mesh 100 can be modified to comprise a plurality of macropores 505, as shown in FIG. 5. These macropores 505 can have an average longest cross-section dimension ranging from about 100 μm to about 2000 μm. In an exemplary embodiment of the present invention, the macropores 505 can have an average longest cross-section dimension of about 1 mm, and these macropores can be spaced approximately 1.5 mm apart. Although not wishing to be bound by any particular theory, it is believed that the macropores 505 facilitate the invasion of vasculature 605 and the migration of cells 610 into the defect site, such as osteoprogenitor cells. (FIG. 6). In modifying a nanofiber mesh 100 to include macropores 505 that facilitate the infiltration of cells osteoprogenitor cells and the invasion of vasculature to the defect site, design considerations include, but are not limited to, the number of macropores 505, the average longest cross-sectional dimension of the macropore 505, the distribution of macropores 505 on the nanofiber mesh 100, and the shape of the macropores 505.

One of skill in the art would realize that the composition and viscosity of the carrier substance 315 may be varied depending upon the composition and design of the nanofiber mesh 100 as well as the composition of the active agent 320. Thus, the carrier substance 315 can further comprise various thickening agents, diluents, and suspending agents to facilitate suspension, retention, and controlled diffusion of the active agent in the carrier substance. For example, active agents may be suspended in a carrier substance that demonstrates reduced viscosity through the use of nanoparticles or microtubes.

Thus, the systems and methods of the present invention contemplate a method for treating a bone defect, comprising adapting a nanofiber mesh to a bone defect of a subject so that the nanofiber mesh substantially conforms to the bone defect, and at least a portion of the nanofiber mesh defines a fillable space; and flowing a carrier substance into the fillable space, the carrier substance comprising a therapeutically effective amount of an active agent.

The phrase "therapeutically effective amount" or "effective amount" as used herein is an amount of a compound that produces a desired therapeutic effect in a subject, such as inducing bone regeneration. The precise therapeutically effective amount is an amount of the composition that will yield effective results in terms of efficacy of treatment in a given subject. This amount (i.e., dosage) may vary depending upon a number of factors, including, but not limited to, the characteristics of the active agent (including activity, pharmacokinetics, pharmacodynamics, and bioavailability), the physiological condition of the subject (including age, sex, disease stage, general physical condition, and responsiveness to a given dosage), the nature of the carrier substance, and the composition of the nanofiber mesh. One skilled in the clinical and pharmacological arts will be able to determine a therapeutically effective amount through routine experimentation, namely by monitoring a subject's response to administration of a compound and adjusting the dosage accordingly.

In an exemplary embodiment of the present invention, a method of treating a bone defect comprises administering a therapeutically effective dose of at least one TGF-β member of the TGF-β superfamily, such as a bone morphogenetic protein (e.g., rhBMP-2, rhBMP-7). In one embodiment, a therapeutically effective amount of bone morphogenetic protein is less than about 100 micrograms per kilogram of body weight of the subject. In another embodiment, a therapeutically effective amount of bone morphogenetic protein is less than about 50 micrograms per kilogram of body weight of the subject. In yet another embodiment, a therapeutically effective amount of bone morphogenetic protein is less than about 25 micrograms per kilogram of body weight of the subject. In still another embodiment, a therapeutically effective amount of bone morphogenetic protein is about 20 micrograms per kilogram of body weight of the subject.

All patents, patent applications, and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure. Therefore, while embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention or the scope of the appended claims.

EXAMPLES

The following examples demonstrate the use of electrospun nanofiber mesh scaffolds for bone regeneration. Nanofiber meshes were utilized in a three-pronged approach. First, nanofiber meshes were validated their ability to robustly support osteogenic cell functions, including proliferation and matrix mineralization. We also demonstrated their efficacy as a cell delivery vehicle. Second, we investigated the effects of modulating nanofiber bioactivity and orientation on stem cell programming. Our results indicate that functionalization of nanofiber meshes with a collagen-mimetic peptide enhanced the migration, proliferation and osteogenic differentiation of cells. Fiber alignment improved cell migration along the direction of fiber orientation. Finally, a nanofiber mesh based hybrid system for growth factor delivery was developed for bone repair and tested in a challenging animal model. The delivery of bone morphogenetic protein (BMP) via this system resulted in the functional restoration of limb function, and in fact proved more efficacious than the current clinical standard for BMP delivery.

The studies performed in this thesis have suggested novel techniques for improving the repair of clinically challenging bone defects. They indicate that delivery of BMP via the hybrid system may reduce the dose and side effects of BMP, thereby broadening the use of BMP based bone augmentation procedures. Therefore, this nanofiber mesh based system has the potential to become the standard of care for clinically challenging bone defects, including large bone defects, open tibial fractures, and nonunions.

Example 1

Colonization and Osteogenic Differentiation of Different Stem Cell Sources on Electrospun Nanofiber Meshes The purpose of this Example was to investigate the attachment, colonization and osteogenic differentiation of human MSCs (hMSCs) and human AFS (hAFS) cells on electrospun nanofiber meshes. This Example demonstrates that electrospun meshes are able to robustly support these functions for both cell types. Compared to tissue culture plastic, there is delayed initial attachment and proliferation, but enhanced mineralization at a later time point. Differences in the kinetics of osteogenic differentiation were observed between hMSCs and hAFS cells. Cell-seeded nanofiber meshes were also effective in colonizing three dimensional scaffolds in an in vitro model. These results provide support for the use of the nanofiber mesh as a cell delivery vehicle for the repair of bone defects in vivo.

Materials and Methods

Fabrication of nanofiber meshes. A polymer solution was made by dissolving 13% (w/v) poly (ε-caprolactone) (PCL) (Sigma-Aldrich, St. Louis, Mo.) in a 40:60 volume ratio of dichloromethane (DCM):dimethylformamide (DMF) (Sigma-Aldrich). PCL pellets were added to the solvent mixture, and gently stirred for 16-24 hours. The polymer solution was loaded in a 3 mL syringe (Becton-Dickinson, Franklin Lakes, N.J.), and a 22 gauge blunt stainless steel needle (Jensen Global Inc., Santa Barbara, Calif.) was attached to the syringe end. The syringe was mounted on a syringe pump (Harvard Apparatus, Holliston, Mass.), and the pump was set to infuse at a rate of 0.75 mL/hr. A flat, 6×6 inch copper plate (McMaster-Carr, Atlanta, Ga.) covered with aluminum foil was used to collect the fibers, and placed at a distance of 20 cm from the needle end. Fibers were electrospun for 50 minutes at a voltage of 14 kV, supplied by a high voltage power supply (Gamma High Voltage Research, Ormond Beach, Fla.), to obtain a thin sheet of nanofiber mesh. To remove any residual solvent, the meshes were placed in a dessicator for at least one day before further use.

Nanofiber mesh morphology. The morphology of the nanofiber meshes was examined using a Scanning Electron Microscope (SEM). A small piece of the dry nanofiber mesh was cut and mounted on a metal stub using double-sided adhesive tape. A thin layer of gold was then deposited on the mesh sample for 80 seconds using a sputter coater (Quorum Technologies, East Granby, Conn.). The gold-coated sample was then viewed under a Hitachi S-800 Field Emission SEM (Hitachi HTA, Pleasanton, Calif.) with 10 kV accelerating voltage. The diameters of the fibers were quantified by analyzing the SEM images (at 7000× magnification) using a custom MATLAB® (MATLAB® 7.0 R14, The MathWorks Inc., Natick, Mass.) program. A total of at least 75 distinct fibers were measured from four randomly chosen locations.

Culture of AFS cells and MSCs. Human amniocentesis cultures were harvested by trypsinization, and subjected to c-kit immunoselection. hAFS cells were subcultured routinely at a dilution of 1:4 to 1:8, and not permitted to expand beyond 70% confluence. The hAFS cells were passaged in aMEM (Minimum Essential Medium Alpha) supplemented with 16% fetal bovine serum (ES Cell-qualified FBS), 100 U/ml penicillin, 100 µg/ml streptomycin, 2 mM L-glutamine (Invitrogen, Carlsbad, Calif.), 18% Chang B and 2% Chang C (Irvine Scientific, Santa Ana, Calif.). In all experiments, cells were used at passages 16-17.

Human MSCs derived from the bone marrow were obtained from the Tulane University Center for Gene Therapy (New Orleans, La.) at passage 1. Cells were isolated using bone marrow aspirates from the iliac crest of normal adult donors. For expansion, these cells were plated at a density of 50 cells/cm$^2$, and cultured in hMSC growth media. The hMSC growth media consisted of aMEM (Invitrogen) supplemented with 16% FBS (Atlanta Biologicals, Atlanta, Ga.), 100 U/ml penicillin, 100 µg/ml streptomycin, and 2 mM L-glutamine (Invitrogen). The cells were subcultured once they reached a confluency of ±70%. Passage 2-3 hMSCs were then used for all experiments.

Cell culture on nanofiber fiber meshes. Square 15 mm samples were cut from nanofiber mesh sheets using scissors. Samples were placed in 24-well culture plates, submerged in 200 proof ethanol (Sigma-Aldrich), and sterilized by allowing the ethanol to evaporate overnight. After the samples had dried completely, they were pre-wetted with sterile 70% ethanol for 30 minutes. The 70% ethanol was then aspirated, and sterile dead weights were placed around the samples to prevent them from floating. The mesh samples were next rinsed three times with excess sterile PBS (Mediatech Inc., Manassas, Va.). An 800 µL volume of media was placed in each well containing the samples. The control groups received hMSC growth media, whereas the osteogenic groups were further supplemented with 10 nM dexamethasone, 6 mM β-glycerol phosphate, 50 µg/ml ascorbic acid 2-phosphate and 50 ng/ml L-thyroxine (Sigma-Aldrich). hMSCs and hAFS cells were then seeded onto nanofiber meshes in approximately 200 µL of hMSC media such that the density of cells was 20,000 cells/cm$^2$. Cells were also cultured in tissue culture treated 24-well plates at the same density for comparison. Media was changed every 3-4 days, and the constructs were cultured for up to 4 weeks.

Cell viability. On days 1, 7, 14 and 28, the viability of the cells in the constructs was assessed using the Live/Dead® staining kit (Molecular Probes, Invitrogen). Harvested constructs were rinsed in PBS and incubated in 4 µM calcein-AM and 4 µM ethidium homodimer-1 for 45 minutes at room temperature. The samples were again rinsed in PBS, and images were obtained on a Zeiss LSM 510 confocal microscope (Carl Zeiss, Thornwood, N.Y.). Green fluorescence of calcein-AM was detected by using a 488-nm Argon ion laser and a band pass 505-550 filter. Red fluorescence of ethidium homodimer-1 was detected by using a 543-nm Helium-Neon laser and a long pass 560 filter.

DNA content. Samples were harvested after 1, 7, 14 and 28 days to evaluate the construct cellularity, which was assessed by determining the DNA content. The cells were first lysed by freeze-thawing the constructs three times in 0.05% Triton X-100 (Sigma-Aldrich) with vigorous vortexing. To freeze the samples, they were placed in dry ice cooled methanol (Sigma-Aldrich) for 5 minutes. Samples were then thawed in a room temperature water bath. The DNA amount in the lysate was quantified using the PicoGreen® dsDNA Quantitation Kit (Molecular Probes, Eugene, Oreg.), and standardized using Lambda DNA solutions of known concentrations. A working solution of the PicoGreen® reagent was made following the manufacturer's protocol, and incubated with experimental samples in the dark for 5 minutes at room temperature. The fluorescence was measured on a plate reader (HTS 7000, Perkins-Elmer, Waltham, Mass.) at an excitation of 485-nm and emission of 535-nm. All samples were run in triplicate, and the DNA content was normalized to the culture surface area of the samples.

Alkaline Phosphatase (ALP) activity. To determine the osteogenic differentiation of the cells on nanofiber meshes, the ALP activity assay was performed. In this assay, the release of p-nitrophenol from p-nitrophenyl phosphate by the ALP enzyme is measured. The same lysate solution that was used to determine DNA content was used for this purpose. The ALP substrate working solution was made by mixing equal parts of 20 mM p-nitrophenyl phosphate, 1.5 M 2-Amino-2-Methyl-1-Propanol (pH 10.25) and 10 mM MgCl$_2$. The experimental samples were mixed with the freshly made substrate working solution, and incubated for 1 hour at 37° C. The reaction was stopped by adding 1N NaOH, and the absorbance was measured at 405 nm on a plate reader (PowerWave XS, Biotek, Vt.). All samples were run in triplicate and compared to p-nitrophenol standards. The ALP activity was normalized by the incubation time and the amount of DNA obtained from the PicoGreen® assay.

Calcium content. To quantify matrix mineralization, the calcium deposited by cells on nanofiber meshes after 28 days was determined using the Arsenazo III dye. Samples were vortexed with 1 N acetic acid overnight to extract the calcium into solution. The extract was mixed with the Arsenazo III reagent (Diagnostic Chemicals Limited, Oxford, Conn.), incubated for 30 seconds at room temperature, and the absorbance read at 650 nm on a plate reader (PowerWave XS, Biotek). The samples were assayed in triplicate and compared to Calcium Chloride (CaCl$_2$) standards.

Calcein staining and quantification. For visualization of the mineral deposited by the cells, the samples were stained using calcein on day 28. Briefly, a stock solution of 100 µg/ml calcein (Sigma-Aldrich) in PBS (pH 7.4) was added to the media on top of the samples, such that the final concentration of calcein was 10 µg/ml. The samples were incubated in the calcein solution for 4 hours in the incubator. After rinsing twice with PBS and fixing with 10% neutral buffered formalin (EMD Chemicals, Gibbstown, N.J.), samples were rinsed with excess of DI water. The fluorescence of the samples was read on a fluorescence plate reader (HTS 7000, Perkins-Elmer) at an excitation of 485-nm and emission of 535-nm. Following this, the same samples were imaged using an inverted microscope (Axio Observer.Z1, Carl Zeiss) and a FITC filter.

Fourier Transform Infrared (FTIR) Spectroscopy. On day 28, constructs were also harvested for analyzing the chemical composition of the mineral deposited on the nanofiber meshes. Samples were dehydrated in 100% ethanol and dried at 50° C. overnight. Acellular PCL nanofiber mesh was used as a negative control. After dehydration, the samples were cut into small pieces, mixed with potassium bromide (Sigma-Aldrich), and pressed into pellets using a custom built apparatus. Samples were analyzed with a Nicolet Nexus 470 FTIR spectrometer (Thermo-Nicolet, Madison, Mich.). Sixty four scans were acquired at 4 $cm^{-1}$ resolution under nitrogen purge.

Cell delivery by nanofiber mesh in vitro. The ability of a cell seeded nanofiber mesh to serve as a cell delivery vehicle was studied using an in vitro model. AFS cells were seeded on to nanofiber mesh samples (15×10 mm) at a density of 200,000 cells/$cm^2$. The cells were allowed to attach to the mesh overnight. On the following day, each cell seeded mesh was wrapped around a cylindrical collagen scaffold (dry dimensions: 4 mm diameter and 9 mm length) aseptically, such that the cells were facing the scaffold. The scaffolds were punched from a fibrous collagen sheet (average pore size 61.7 µm, 93.7% pore volume, Kensey Nash, Exton, Pa.). The mesh was held in position by placing two interrupted silk sutures through the mesh and scaffold at the two ends of the scaffold. For comparison, we also seeded 300,000 cells throughout collagen scaffolds by pipetting the cell suspension directly in the scaffolds. There was no nanofiber mesh in this control group. The constructs were statically cultured in hAFS cell growth media. After two weeks, the mesh was taken off, following which the mesh and scaffold were stained with the Live/Dead® staining kit (Molecular Probes, Invitrogen) to visualize the cell migration into the scaffold. A confocal microscope (Zeiss LSM 510, Carl Zeiss) was used to take serial images to create three dimensional images.

Data analysis. Results are presented as mean±standard error of the mean (SEM). Analysis of variance (ANOVA) was performed on data, with pairwise comparisons done using the Tukey multiple comparison procedure. A p-value<0.05 was considered significant. Residuals were used for diagnosing the appropriateness of the model by analyzing the constancy of error variance and normality of error terms. Wherever required, remedial measures were taken by transforming the data according to the Box-Cox procedure, or by using weighted least squares to make the error variance constant and the error distribution normal Minitab® 15 (Minitab Inc., State College, Pa.) was used to perform the statistical analysis.

Results

Morphology of nanofiber meshes. PCL nanofiber meshes were electrospun on a flat collector plate. The mesh formed a circular area of approximately 8 cm diameter. The thickness of the mesh was found to vary with location, with the central areas thicker than the edges. The thin mesh samples from the edges were discarded and not used for cell culture. Fibers appeared to be smooth and uniform, with minimal bead formation (FIGS. 7A and &B). The quantification of the fiber diameter using a custom MATLAB® program demonstrated that the mean fiber diameter was 591 nm with a standard deviation of 199 nm. The fiber diameter histogram revealed that most of the fibers were between 300-900 nm, with the highest frequency occurring in the 500-600 nm range (FIG. 7C).

Viability and colonization of hMSCs and hAFS cells over time. hMSCs and hAFS cells were seeded on electrospun nanofiber meshes and tissue culture plates, and cultured in osteogenic media for up to 28 days. The viability of the cells on the meshes was assessed on days 1, 7, 14 and 28 by the Live/Dead® staining kit. The live cells are stained green, whereas the dead cells appear red. At the same time points, DNA from the samples was extracted and quantified to estimate the number of cells on the meshes, as well as in the culture wells. The Live/Dead images illustrate that both cell types attached to the nanofiber meshes by day 1 and were able to spread out by day 7. During days 7-14 the number of cells increased considerably, and by day 28, the cells were confluent on the meshes. The viability of both cell types on the meshes was found to be high, as seen by the extensive green stain, though a few dead cells were detected. No differences were observed in the viability and colonization between the two cell types.

The DNA quantification over the four week culture period was used to compare the colonization kinetics of the two cell types on tissue culture plates and nanofiber meshes, respectively (FIGS. 8A-D). There was significant increase in DNA with time for both cell types, on plates as well as meshes, indicating cellular proliferation. On plates, the number of hAFS cells increased between days 1-7 but did not change significantly after that, suggesting rapid initial proliferation and confluency around day 7 (FIG. 8A). On the other hand, hMSCs increased in numbers between both days 1-7 and days 14-28. However, this result is an artifact of hMSC culture on the plates, as the hMSCs were found to lift off the plate after confluence around day 7 to form a pellet, and then repopulate the plate. This pelleting behavior was not seen with the hAFS cells for up to 28 days, though the hAFS cells do ultimately lift off the plate. The hMSC repopulation explains the increase in hMSC cell number between days 14-28 and the differences seen between hMSCs and hAFS cells on days 14 and 28. There were also significantly more hAFS cells than hMSCs on day 1, suggesting a higher initial attachment and/or proliferation rate.

The pelleting phenomenon does not occur on the nanofiber meshes, even at a later time points. There was a significant increase in DNA for both cell types between days 1-7, and an even higher increase between days 7-14, corresponding to the Live/Dead images (FIG. 8B). The number of cells did not change significantly after that, suggesting confluency of the cells on the nanofiber meshes. There were no significant differences in the DNA between hMSCs and hAFS cells at any time point.

The colonization kinetics of hAFS cells on the nanofiber meshes was also compared with that on the tissue culture plates (FIGS. 8C-D). On days 1, there was significantly less DNA on the mesh compared to plates, suggesting that not all cells attach to the nanofibers within the first 24 hours. The same trend was seen on day 7. However, by day 14, there was no significant difference between meshes and plates. On day 28, there was again no significant difference, though the lines crossed over. Although the hMSCs pellet in the plates and repopulate the culture surface by day 28, the amount of DNA was not significantly different than that on the mesh.

Osteogenic differentiation of hMSCs and hAFS cells: ALP activity. The osteogenic differentiation of the cells was first investigated by analyzing the ALP activity of the cells (FIG. 9). ALP is a membrane-bound enzyme that hydrolyzes phosphate esters, which results in inorganic phosphate being available for incorporation into mineral deposits. There was significant increase in the ALP activity of both cell types with time, on plates as well on nanofiber meshes, suggesting osteogenic differentiation. On tissue culture plates, ALP activity peaked at day 7 for MSCs, whereas for AFS cells it increased slowly but continuously up to day 28 (FIG. 9A). Interestingly, the maximum ALP activity of the hAFS cells was greater than the hMSC peak. On the nanofiber meshes, hMSCs demonstrated a similar earlier rise in ALP activity, on day 14, compared to day 28 for hAFS cells (FIG. 9B). The ALP activity of the hMSCs was significantly greater than that of hAFS cells on all time points other than day 1. The ALP response on meshes is delayed compared to that on the plate, as seen by the later increase in ALP activity. Interestingly, the ALP activity of hMSCs on meshes was sustained longer than plates, with the maximum value on meshes at day 28 greater than that observed on plates at day 7 ($p<0.05$).

Osteogenic differentiation of hMSCs and hAFS cells: matrix mineralization. The osteogenic differentiation of the cells was further investigated by quantifying and staining the calcium deposits and by analyzing the chemical nature of the deposited mineral by FTIR spectroscopy. An ANOVA on the calcium deposited by the cells revealed that both cell type and the culture surface had a significant effect on the calcium levels (FIG. 10). Under osteogenic stimulation, all groups demonstrated increased calcium deposition, compared to growth media, indicating that cells are able to differentiate to an osteoblastic phenotype on the surfaces. Calcium levels in the hMSC growth media groups were negligible. hAFS cells deposited a higher amount of calcium than hMSCs on both plates and meshes. Also, both cell types deposited more calcium on meshes compared to plates.

FTIR spectroscopy was used to characterize the composition of the mineral that was deposited by the cells on the nanofiber meshes under osteogenic stimulation. To distinguish the peaks associated with the mineral from the peaks associated with the PCL mesh, an acellular piece of PCL mesh was also scanned. The cellular samples displayed amide I/II peaks at 1655 and 1550 $cm^{-1}$, a carbonate peak at 870 $cm^{-1}$, and a doublet split phosphate peak at 560 and 605 $cm^{-1}$, which were not seen in the acellular mesh. There was also a peak at 1050 $cm^{-1}$ in the cellular samples, but it overlapped with a PCL mesh peak. These peaks are the signature of a carbonate-containing, poorly crystalline hydroxyapatite, the form of mineral that is found in native bone. This suggests that both hMSCs and hAFS cells deposited mineral that possessed the characteristic bands of physiological mineral.

Samples were stained with calcein to visualize the presence of calcium on the nanofiber meshes. The calcein staining demonstrated the presence of extensive calcium-containing mineral nodules, which were uniformly distributed on the meshes. This was the case in both the hMSC and hAFS cell osteogenic groups, whereas the growth media groups stained minimally. Quantification of the fluorescence revealed that more mineral was deposited by the hAFS cells compared to the hMSCs (FIG. 11), thus supporting the calcium data.

Nanofiber mesh as a cell delivery vehicle. As a preliminary evaluation of the nanofiber mesh for cell delivery, AFS cells were seeded on nanofiber meshes and wrapped around cylindrical collagen scaffolds in vitro. The constructs were cultured for two weeks and then stained with the Live/Dead® staining kit. In the cell-seeded scaffold, more cells were present at the periphery of the scaffold, even though cells were seeded throughout. A large number of dead cells were also detected in the interior of the scaffold. When the cell-seeded mesh was wrapped around a collagen scaffold, we found that numerous cells had migrated off the mesh onto the collagen scaffold and had high viability. The majority of cells were located close to the peripheral surface. Interestingly, we noted that the top surface was completely covered with cells. This implies that the cells were able to migrate at least 2 mm from the edge, where the mesh was present, to the center of the top surface. A few cells were also seen in the interior of the scaffold, more than 500 µm away from the peripheral surface. The mesh was completely confluent with cells indicating that only a subset of cells migrates from the mesh onto the scaffold.

Example 2

Nanofiber Orientation and Surface Functionalization Modulate Human MSC Infiltration and Osteogenic Differentiation Electrospun nanofiber meshes are a unique type of scaffold with structural features that, at least by scale, resemble the extracellular matrix (ECM). In addition, they exhibit large surface area and high porosity, making them suitable as a scaffold for guiding tissue regeneration by host cells. For example, in the case of a large diaphyseal bone defect, the nanofiber mesh may be able to provide cues for progenitor cells from the periosteum and marrow space to migrate into the defect region and deposit mineralized matrix. Example 1 demonstrated that nanofiber meshes made from a synthetic polymer are able to support the attachment, colonization and osteogenic differentiation of progenitor cells. Synthetic polymers, however, lack biological ligands, and are not capable of directing intracellular signaling and response. Nanofiber meshes have also been fabricated from natural materials like collagen and fibrinogen, but these are limited by poor mechanical strength and handling characteristics for in vivo applications. Approaches that incorporate bioactive molecules within a synthetic polymer backbone may provide an optimal combination of biological activity and mechanical integrity.

Tremendous advances have been made in imparting biofunctionality to synthetic materials by coating them with ECM components. These biomimetic material surfaces present adhesion motifs to engage the cell signal transduction machinery for directing cellular response and tissue repair. Though adhesive proteins such as type I collagen, fibronectin and laminin have been immobilized on material surfaces, these approaches are limited by protein purification and processing issues, and a potential host immunogenic response. In addition, the multiple adhesion domains in a full-length protein may trigger conflicting intracellular signals, leading to suboptimal tissue repair. Therefore, there is a great need to develop peptides that mimic specific domains of natural proteins. These ECM-mimetic peptides can be synthesized and purified with relative ease, and furthermore, can be designed to trigger a specific cellular response. One such peptide that has been recently investigated is a triple-helical, collagen-mimetic oligopeptide containing the glycine-phenylalanine-hydroxyproline-glycine-glutamate-arginine (GFOGER) domain from residues 502-507 of the $α_1(I)$ chain of type I collagen. It has been shown that the interaction of this adhesion motif with $α_2β_1$ integrin mediates osteoblast adhesion, differentiation and matrix mineralization. This has been exploited to enhance the adhesion and osteogenic differentiation of progenitor cells and improve implant integration, by coating surfaces with the GFOGER peptide. This technique utilizes simple adsorption of the GFOGER peptide on implant surfaces in physiologic conditions, which may be advantageous for clinical translation.

Another set of guidance strategies consists of topographical cues to influence cellular responses. It is now accepted that surface morphology, including roughness and texture, modulates cellular response. For instance, titanium implants with rough microtopographies reduced cell number, increased differentiation and enhanced implant integration. The electrospinning process can be easily adapted to obtain fibrous matrices with varying structure. Fiber alignment, especially, has generated significant interest due to the fact that a number of native and regenerating tissues display an ordered architecture. Studies have shown that alignment of fibers along a particular direction affects cellular attachment and morphology as well as matrix deposition. Neurites grown on aligned nanofibers display contact guidance and improved migration. However, the effect of fiber alignment on human MSCs (hMSCs) function needs to be investigated. In addition, the combined effect of nanofiber mesh orientation and surface composition has not been studied extensively.

The purpose of this study was to investigate the effect of nanofiber functionalization and orientation on hMSC function, in order to identify conditions that best support bridging of bone defects by osteoprogenitor cells. Nanofiber meshes were functionalized with the GFOGER peptide to improve cell adhesion and osteogenic differentiation. An oriented topography was obtained by electrospinning aligned nanofibers in order to enhance cellular migration. An in vitro model was developed to examine hMSC infiltration on top of nanofiber meshes, and isolated the contribution of cell proliferation versus migration. The individual and combined effects of nanofiber functionalization and orientation on hMSC function were investigated. In addition, the efficacy of GFOGER coating to improve nanofiber mesh based repair of segmental bone defects in vivo was assessed Materials and Methods Electrospinning and nanofiber mesh characterization. Nanofiber meshes were made by electrospinning, and characterized as described in Example 1. Briefly, a 12% (w/v) solution of poly (ε-caprolactone) (PCL) was made in a 90:10 volume ratio of hexafluoro-2-propanol (HFP):dimethylformamide (DMF) (Sigma-Aldrich, St. Louis, Mo.). A 3 mL syringe (Becton-Dickinson, Franklin Lakes, N.J.) was filled with the PCL solution and fitted with a 22 gauge blunt-end needle (Jensen Global Inc., Santa Barbara, Calif.). The syringe was placed on a syringe pump (Harvard Apparatus, Holliston, Mass.), which was adjusted for a flow rate of 0.75 mL/hr. To create a nanofiber mesh with random fiber alignment (random nanofiber mesh), a flat copper plate was placed at a distance of 20-23 cm from the needle tip. To obtain meshes with fibers aligned along the same direction (aligned nanofiber mesh), they were collected on a mandrel rotating at ~2500 rpm and placed 8-10 cm from the need tip. The syringe needle was attached to the positive end of a high voltage power supply (Gamma High Voltage Research, Ormond Beach, Fla.), and the collector was grounded to create the electrostatic field required for electrospinning. After applying a voltage of 13-20 kV, the polymer solution was ejected from the needle towards the collector and deposited as nano-scaled fibers. The fibers were collected for 45-60 minutes to obtain meshes with sufficient thickness for cell culture experiments.

The nanofiber meshes were sputter coated with gold (Quorum Technologies, East Granby, Conn.) and their morphology visualized by Scanning Electron Microscopy (SEM; Hitachi HTA, Pleasanton, Calif.). A custom MAT-LAB® (The MathWorks Inc., Natick, Mass.) program was used to calculate the individual fiber diameter from the SEM images. The alignment of the fibers in aligned nanofiber meshes was quantified by measuring fiber angle relative to the direction of rotation, using the Image-Pro software (Media Cybernetics, Inc., Bethesda, Md.). In the case of random nanofiber meshes, the angles were measured with respect to an arbitrarily set line.

GFOGER peptide preparation and nanofiber surface coating. The peptide, GGYGGGPC(GPP)$_5$GFOGER(GPP)$_5$GPC, was synthesized by the Emory University Microchemical Facility (Atlanta, Ga.). This peptide contains the GFOGER motif, where 0 refers to hydroxyproline. The purified peptide was lyophilized as a trifluoroacetic acid (TFA) salt. The peptide was reconstituted at a concentration of 10 mg/mL in a 0.1% TFA solution containing 0.01% sodium azide (NaN$_3$). The stock solution was diluted to 50 µg/mL in phosphate-buffered saline (PBS, Mediatech Inc., Manassas, Va.). Nanofiber mesh samples were sterilized by ethanol evaporation, wetted with 70% ethanol and rinsed with excess PBS. The samples were then passively adsorbed with GFOGER by submerging them in the dilute GFOGER solution for 2 hours at room temperature or overnight at 4° C. For comparison, samples were also coated with a 50 µg/mL purified rat type I collagen (Trevigen Inc., Gaithersburg, Md.) solution or left uncoated in PBS. After rinsing again with PBS to remove any unbound peptide, the samples were ready for analysis or cell seeding.

Analysis of GFOGER surface coating. The GFOGER adsorbed on the surface of the nanofibers was visualized and quantified using a biotinylated version of the GFOGER peptide. Biotin was conjugated to the carboxyl end of the peptide using the EZ-Link® Amine-PEG$_3$-Biotin kit (Pierce Biotechnology), and the unreacted biotin was removed by dialysis. To visualize the presence of the peptide on the nanofiber surface, the GFOGER coated nanofiber mesh samples were incubated with 10 µg/mL fluorescein conjugated NeutrAvidin® (Molecular Probes, Eugene, Oreg.) for 30 minutes at room temperature in the dark. After rinsing with excess PBS, images were taken on an inverted fluorescence microscope (Axio Observer.Z1, Carl Zeiss, Thomwood, N.Y.) using a FITC filter. The saturation of the surface by GFOGER was investigated by incubating meshes with varying GFOGER concentrations of 0-50 µg/mL. To quantify the amount of the biotinylated GFOGER peptide adsorbed on the nanofiber surface, an ELISA was performed using an anti-biotin antibody. Non-specific adsorption of the antibody was first blocked by immersing the nanofiber meshes in 0.25% heat denatured serum albumin with 0.0005% Tween-20, 1 mM EDTA, and 0.025% NaN$_3$ in PBS for 1 hour at 37° C. The meshes were then incubated with an anti-biotin antibody (diluted 1:2000) conjugated to alkaline phosphatase (clone BN-34, Sigma-Aldrich) for 1 hour at 37° C. An alkaline phosphatase substrate, 4-methylumbelliferyl phosphate, was used at a concentration of 60 µg/mL in diethanolamine buffer (pH 9.5) to measure the amount of bound antibody. After incubating the meshes with the substrate solution for 1 hour at 37° C., the fluorescence was read on a plate reader (HTS 7000, Perkins-Elmer, Waltham, Mass.) at an excitation of 360 nm and emission of 465 nm.

Human mesenchymal stem cell (hMSC) culture. Briefly, bone marrow aspirates were taken from the iliac crest of normal adult donors, the nucleated cells were isolated with a density gradient and only the cells that adhered to the plate after 24 hours were cultured further. Passage 1 cells frozen in 1 mL aliquots were shipped us. To expand a culture, the cells were thawed and plated at a density of 50 cells/cm$^2$ in αMEM (Invitrogen), supplemented with 16% FBS (Atlanta Biologicals, Atlanta, Ga.), 100 U/ml penicillin, 100 µg/ml streptomycin, and 2 mM L-glutamine (Invitrogen). This is termed the hMSC growth media. After the cells reached a confluency of ~70%, they were harvested with 0.25% trypsin-EDTA (Invitrogen), counted, and either expanded again or seeded on nanofiber meshes. Passage 2-3 hMSCs were used in all experiments.

Figure 12:
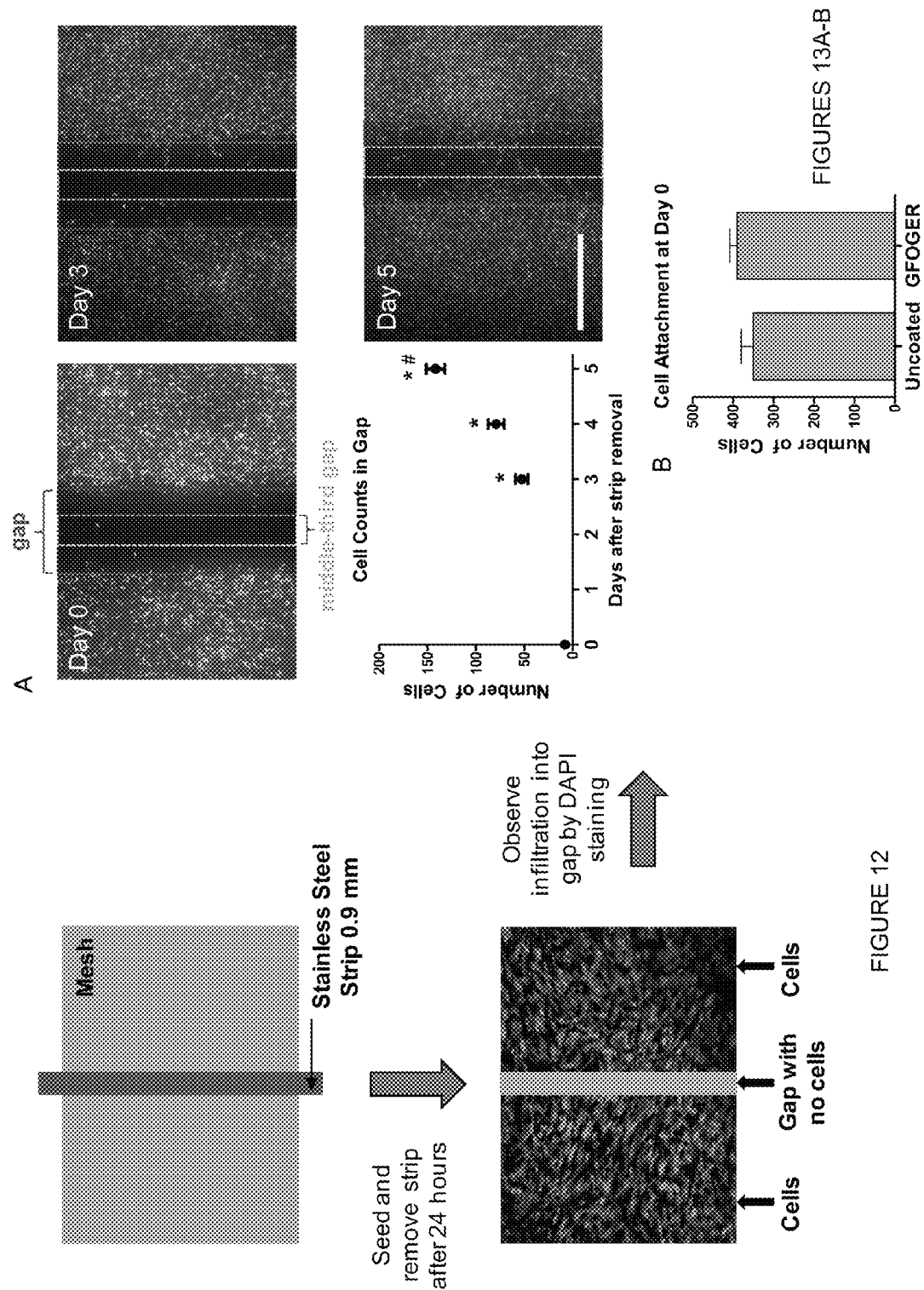
FIG. 12 is a schematic of the cell infiltration model.

Investigating cell infiltration on nanofiber meshes in an in vitro model. Rectangular samples (8 mm×12 mm) were cut from random and aligned nanofiber mesh sheets, sterilized and coated with GFOGER or collagen, or left uncoated in 24-well tissue culture plates, as mentioned above. A 0.9 mm wide sterile stainless steel strip was then placed on the nanofiber mesh to create a region without cells (FIG. 12). For aligned nanofiber meshes, the strip was placed perpendicular to the fiber orientation. Samples were submerged in 800 µL of hMSC growth media, after placement of a dead weight on the edges to prevent them from floating. hMSCs were then seeded on the nanofiber mesh samples at a density of 40,000 cells/cm$^2$ in 200 µL of hMSC growth media. After 24 hours, the strip was removed, and the cell infiltration into the gap was observed at various time points.

Cell infiltration was analyzed by staining the nuclei with 4',6-diamidino-2-phenylindole (DAPI, Molecular Probes). Some samples were, in addition, stained with rhodamine phalloidin (Molecular Probes) to visualize the cell alignment. After samples were taken down, they were rinsed with PBS and fixed with 4% formaldehyde for 10 minutes. The samples were then incubated in 0.05% Triton-X (Sigma-Aldrich) for 5 minutes, rinsed in PBS and incubated in 5 units/mL rhodamine phalloidin for 20 minutes. After a PBS rinse step, the samples were incubated in 5 µg/mL DAPI for 5 minutes. Samples were finally washed in excess PBS to remove any unbound dye, and images were taken on an inverted fluorescence microscope (Carl Zeiss). The DAPI images were further processed using ImageJ (U.S. National Institutes of Health, Bethesda, Md.) to count the cell nuclei, and thereby quantify cell number. Three fields of view along the gap were analyzed for each sample, and the mean cell number per field is presented, along with the standard error of the mean. To investigate the number of cells attached on day 0, four locations outside the gap were analyzed.

Role of cell proliferation in the cell infiltration model. To investigate whether cell proliferation influences the infiltration of cells on nanofiber meshes, mitomycin C was used to block proliferation. Mitomycin C, which is a known inhibitor of cell proliferation, cross links the strands of DNA, thereby inhibiting DNA replication. The effect of mitomycin C on hMSC proliferation was first studied on tissue culture plates. hMSCs were plated at a density of 20,000 cells/cm$^2$, and after 24 hours, they were incubated with 10 µg/mL mitomycin C for 60 minutes. Control samples remained in culture media. Cell proliferation was assessed using 5-bromo-2'-deoxyuridine (BrdU) labeling, according to the manufacturer's instructions (FLUOS, Roche Diagnostics, Mannheim, Germany). Forty eight hours after cell seeding, the cells were incubated in hMSC growth media containing 10 µM BrdU for 24 hours in the incubator. Cells were fixed with an ethanol based fixative for 45 minutes, and denatured with 4 M HCl for 20 minutes to allow for antibody access. After neutralizing the pH with PBS, the cells were incubated with a monoclonal anti-BrdU-antibody conjugated with fluorescein for 45 minutes at 37° C. The cells were finally stained with DAPI for the total number of cells and analyzed using fluorescence microscopy, as mentioned above. Nine fields were examined in a 3×3 grid pattern, and the number of BrdU positive cells along with the DAPI stained cells were counted. Data are presented as the BrdU and DAPI cell counts, as well as the proportion of BrdU positive cells.

The effect of mitomycin C was next studied in the cell infiltration model on nanofiber meshes. Cells were seeded on rectangular nanofiber mesh samples at a density of 40,000 cells/cm$^2$, as above. Twenty four hours post seeding, mitomycin C was added to the media at a final concentration of 10 µg/mL, and incubated for 60 minutes. The media was slowly aspirated, fresh media was added and the stainless strip was removed. After a further 48 hours, the samples were taken down, stained with DAPI and analyzed for cell infiltration into the gap.

Osteogenic differentiation and total DNA content on nanofiber meshes. Random and aligned nanofiber mesh samples were coated with GFOGER, collagen, or left uncoated. hMSCs were seeded on circular mesh samples (diameter: 12 mm), cut using biopsy punches (Acuderm, Ft. Lauderdale, Fla.), at a density of 20,000 cells/cm$^2$. Four days after seeding, the hMSC growth media was replaced with osteogenic media, which consists of the hMSC growth media supplemented with 10 nM dexamethasone, 6 mM β-glycerol phosphate, 50 µg/ml ascorbic acid 2-phosphate and 50 ng/ml L-thyroxine (Sigma-Aldrich). Media was changed every 3-4 days and the samples were cultured for 3 weeks. The samples were analyzed for DNA content, alkaline phosphatase (ALP) activity and calcium deposition, as described previously in Example 1. Briefly, cells were lysed by freeze-thawing three times. The cell extract was used to measure DNA amount by the PicoGreen® dsDNA Quantitation Kit (Molecular Probes) and ALP activity by the use of p-nitrophenyl phosphate. The calcium content of a separate set of mesh samples was determined by using the dye Arsenazo III, after overnight incubation in 1 N acetic acid.

Assessment of GFOGER coated nanofiber meshes in vivo. Nanofiber meshes were used to create tubular implants, having a diameter of approximately 5 mm and a length of 13 mm, without any perforations. The mesh tubes were coated with 50 µg/mL GFOGER overnight at 4° C., while control samples were left in PBS. Female Sprague-Dawley rats aged 13 weeks were used for this study. Both femurs were stabilized by fixation plates, and 8 mm segmental defects were created in the mid-diaphyses. Nanofiber mesh tubes were rinsed with PBS, and implanted in the defect, such that the periphery of the defect was covered with nanofiber mesh with the center empty.

Radiographs were obtained at 4 and 12 weeks, and ex vivo µCT analysis was performed at 12 weeks to detect bone formation. Torsional testing was performed on extracted femurs at 12 weeks to test their biomechanical properties. Histological analysis consisted of embedding in glycol methacrylate (GMA), obtaining 5 µm sections, and staining with H&E.

Data analysis. Data were analyzed using ANOVA and Tukey's tests for pairwise comparisons. Whenever required, the raw data was transformed using a natural logarithmic transformation to make the data normal and the variance independent of the mean. Student's t-test was used for 2-sample comparisons, where it was appropriate. Other statistical tests that were performed for specific comparisons are mentioned in the results section. The significance level for the above analyses was set at p<0.05. Minitab® 15 (Minitab Inc., State College, Pa.) was used for all statistical analysis.

Results

Nanofiber mesh morphology and alignment. PCL nanofiber meshes were produced by electrospinning and characterized by analyzing SEM images. Interconnected, nonwoven fibers that were mostly bead-free were obtained (FIG. 1). The resulting nanofiber mesh is a porous structure, but due to the multiple fiber layers, the effective pore size appeared to be less than 2 µm, much less than hMSC dimensions. A flat stationary collector was used to obtain random nanofiber meshes with no dominant fiber orientation. The mean and median fiber diameters for random meshes were found to be 168.0 nm and 122.8 nm respectively. The distribution of fiber diameters indicated that the highest frequency occurred for fibers between 75 nm to 125 nm, with 90% of the fibers between 50-300 nm. To obtain aligned nanofiber meshes, a rotating mandrel was used to orient the fibers along the direction of rotation of the mandrel surface (FIG. 2A). In this case, the mean and median fiber diameters were observed to be 256.4 nm and 227.4 nm. The fibers of the aligned meshes were found to be significantly larger in diameter than those in the random meshes (Mann-Whitney test; $p<0.001$). The angle of the fibers with respect to an arbitrary line was measured to quantify fiber alignment (FIG. 2B). Though there is a moderate spread in the orientation of the fibers, a preferred fiber direction was observed, with 89% of the fibers between −45 to 45°. For random meshes, this metric was calculated to be only 52%. Using a Z test for proportions, the alignment was found to be significantly higher in the case of aligned meshes ($p<0.0001$). hMSCs seeded on aligned nanofiber meshes exhibited a polarized morphology along the preferred fiber direction, while in the case of random nanofiber meshes, the cells did not display any regular orientation (FIG. 3C).

GFOGER coating of nanofiber meshes. The collagen-mimetic peptide: $GGYGGGPC(GPP)_5GFOGER(GPP)_5GPC$, containing the GFOGER motif, was synthesized by stepwise solid-phase procedures. The amino acid sequences adjacent to GFOGER enable formation of a stable right-handed triple helical configuration, which is required for cell adhesion. The GFOGER peptide was passively adsorbed on the surface of nanofiber meshes at a concentration of 50 µg/mL. The adsorbed peptide was visualized by coating the meshes with a biotinylated GFOGER peptide and incubating in a fluorescein conjugated NeutrAvidin®. The images revealed that the peptide coated the individual fibers uniformly over the entire mesh area. An ELISA was performed to quantify the amount of the GFOGER peptide adsorbed on the nanofibers with varying peptide concentration. The saturation curve indicated that the relative surface density increased with increasing peptide concentration, with the surface being saturated at a concentration of approximately 20 µg/mL. The peptide concentration at which the surface is 50% saturated, was calculated to be 3.45 µg/mL. For all further experiments, a peptide concentration of 50 µg/mL was used to ensure saturation of the surface for maximal biologic response.

Cellular infiltration on nanofiber meshes. An in vitro model was developed to study the effect of GFOGER coating and fiber alignment on cellular infiltration on top of nanofiber meshes. A cell-free region was created on the mesh, and the infiltration of hMSCs into this gap was examined by analyzing the DAPI stained images. To observe baseline infiltration, we first performed the experiments with uncoated, random nanofiber meshes (FIG. 13A). A cell-free region was generated in day 0 samples. The mean gap width was found to be 0.874±0.02 mm, which was slightly less than the width of the stainless steel strip (0.9 mm). The number of cells in the gap were counted on days 0, 3, 4 and 5. The cell count in the gap was found to be negligible on day 0. The quantification of cell infiltration revealed that there were significantly more cells in the gap on days 3 and 4 compared to day 0, and on day 5 compared to days 3 and 4 ($p<0.05$). The gap was not completely confluent with cells, even at day 5, indicating a slow infiltration rate on the uncoated and random nanofiber meshes. To investigate whether GFOGER coating had a significant effect on cell attachment efficiency, we counted the cells that attached outside the gap on day 0. The cell counts were observed to be equivalent in both the uncoated and GFOGER coated groups, indicating that GFOGER coating did not modify the cell attachment efficiency (FIG. 13B). This implies that both sets of samples start with comparable number of cells on the gap border.

The ability of GFOGER coating and fiber alignment to enhance cellular infiltration in this model was next studied on day 2 after strip removal. Some samples were coated with collagen to compare to the collagen-mimetic GFOGER peptide. The DAPI images revealed that the gaps on the GFOGER coated meshes were completely confluent with cells. Aligned and collagen coated meshes displayed moderately more cell infiltration than random and uncoated meshes, respectively. The cell numbers were determined in two regions: the entire gap and the middle-third of the gap. The middle-third region of the gap was analyzed as a more stringent measure of cellular infiltration. Analysis of the cell counts indicates that both coating and fiber alignment had a significant effect on cell infiltration in both the regions (FIG. 14). In the entire gap region on random meshes, GFOGER coated samples displayed higher cell numbers, compared to both uncoated and collagen samples. On the aligned meshes, both GFOGER and collagen coated samples had higher cell counts than the uncoated samples. Fiber alignment enhanced cell infiltration on uncoated and collagen coated samples. However, this effect was not seen on the GFOGER coated meshes, probably due to the fact that the gap was saturated with cells, even on the GFOGER coated, random meshes. Analysis of the middle-third region of the gap revealed that the cell counts displayed the following order for both random and aligned meshes: GFOGER>Collagen>Uncoated. Fiber alignment enhanced the cell infiltration on both uncoated and collagen coated samples, similar to the observation in the entire gap.

Effect of cell proliferation on the infiltration of cells on nanofiber meshes. The cell infiltration observed on nanofiber meshes could be due to the migration and/or proliferation of hMSCs. To assess the contribution of cell proliferation, proliferation was blocked by treating the cells with mitomycin C, a known inhibitor of cell proliferation, 24 hours after seeding. Mitomycin C was verified to inhibit proliferation of hMSCs on tissue culture plates by staining with BrdU, a marker of cell proliferation. The results demonstrate that 48 hours after mitomycin incubation, the number of proliferating cells (seen with BrdU staining) decreased, thereby reducing the total number of cells (seen with DAPI staining) at this time point. In the absence of mitomycin C, the proportion of proliferating cells during the 24 hour period was 84.1%. This proportion decreased significantly to 6.4% in the presence of mitomycin C, indicating that mitomycin C blocked proliferation in almost all hMSCs.

The effect of inhibiting cell proliferation on the infiltration of hMSCs on nanofiber meshes was next investigated. hMSCs were seeded on nanofiber meshes, with a stainless steel strip placed on top, and allowed to attach for 24 hours (FIG. 15A). The cells were incubated with mitomycin C for 60 minutes, and the strip was removed. After 48 hours of strip removal, the samples were stained with DAPI and analyzed for cell infiltration (FIG. 15B). The analysis of both the entire gap and the middle-third gap regions revealed that in the absence of mitomycin C, both GFOGER coating and fiber alignment enhanced cell infiltration, as observed before. With mitomycin C incubation, the overall cell infiltration decreased, indicating that cell proliferation contributed significantly to the infiltration. In the presence of mitomycin C, only the aligned, uncoated mesh samples had a significantly higher cell count than the random, uncoated mesh samples, in the entire gap region. In contrast, in the middle-third of the gap, the random, GFOGER-coated samples demonstrated significantly higher infiltration than the random, uncoated samples. Furthermore, the aligned, uncoated group displayed a higher cell count than the random, GFOGER-coated group. These results suggest that both cell proliferation and migration contribute to the observed cell infiltration on meshes, and that proliferation has a larger influence on infiltration due to GFOGER coating, compared to fiber alignment.

Influence of nanofiber coating and alignment on total DNA content and osteogenic differentiation. Cells were seeded on circular nanofiber meshes and cultured in either hMSC growth or osteogenic media up to 21 days. This culture system does not involve the use of a stainless steel strip, and the cells are uniformly distributed on the mesh. First, the effect of GFOGER coating on changes in cell number was studied by measuring the amount of DNA extracted from the samples at days 4 and 7. The results demonstrate that GFOGER coating increased the amount of DNA in osteogenic media samples at both days 4 and 7, suggesting an improved proliferation rate (FIG. 16). GFOGER coating did not have a significant effect on amount of DNA in growth media. The effect of coating and fiber alignment on DNA content in osteogenic media was investigated at a later time point of 21 days. ANOVA revealed that coating had an overall significant effect on amount of DNA, but there were no significant individual differences between the groups (FIG. 17A).

The influence of nanofiber coating and alignment on the osteogenic differentiation of hMSCs in osteogenic media was studied by measuring the ALP activity and calcium deposition. Analysis of the ALP activity data revealed that both coating and fiber alignment had a significant effect on ALP activity, and that the GFOGER-coated samples displayed an overall higher ALP activity than the uncoated and collagen coated groups (FIG. 17B). In the case of random nanofiber meshes, the GFOGER group also demonstrated significantly higher ALP activity than the uncoated and collagen groups, whereas, on aligned meshes, the GFOGER group displayed significantly higher activity than the collagen group only. Fiber alignment was found to reduce the ALP activity, in the case of GFOGER- and collagen-coated samples.

Under osteogenic stimulation, hMSCs deposited calcium on the nanofiber meshes, indicative of an osteoblast phenotype (FIG. 17C). GFOGER coating significantly enhanced calcium deposition on both random and aligned meshes, compared to uncoated meshes. In addition, on random meshes, GFOGER-coated samples demonstrated significantly higher calcium deposition than collagen-coated samples. Collagen coating increased calcium levels only in the case of aligned meshes. Fiber alignment did not have an overall significant effect on calcium deposition, though a reduction was observed in the case of uncoated meshes.

Figure 18:
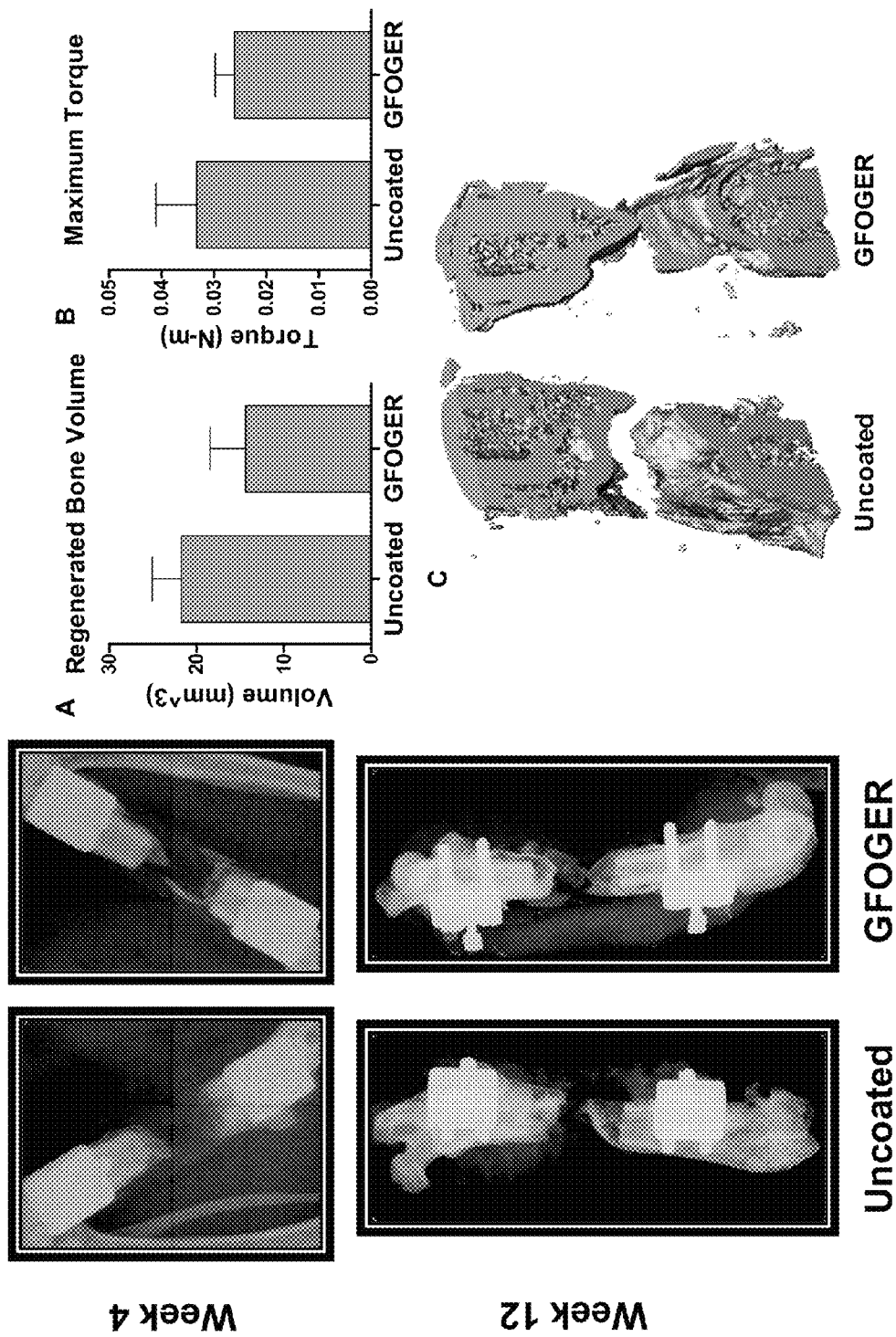
FIG. 18 is radiographs of femurs implanted with nanofiber mesh tubes at 4 and 12 weeks.

Assessment of GFOGER coated nanofiber meshes in vivo. To investigate the ability of GFOGER coated nanofiber meshes to enhance bone formation in vivo, tubes made from nanofiber meshes were coated with the GFOGER peptide, or left uncoated, and implanted around segmental bone defects created in rat femurs. Radiographs at 4 and 12 weeks displayed new bone formation near the ends and the periphery of the defect (FIG. 18). However, none of the defects were bridged completely. The results of the μCT analysis and torsional testing at 12 weeks revealed no significant differences between the two groups, indicating that coating nanofiber mesh tubes with GFOGER did not enhance bone formation in this model (FIG. 19). The cross sectional views of the μCT images illustrated some bone formation along the nanofiber mesh tube and at the native bone boundary. However, capping of defect ends was observed, and presence of bony tissue was not evident at the defect center. Histological analysis of the defect area confirmed capping of the defect ends with newly formed bone (FIG. 20). A combination of newly formed bone, fibrous tissue and marrow was seen within the defect.

Example 3

A Novel Hybrid System for Growth Factor Delivery Promotes Functional Repair of Large Bone Defects The primary objective of this Example was to develop and test a hybrid growth factor delivery system for bone repair that utilizes an electrospun nanofiber mesh and injectable alginate hydrogel. To test this system, we evaluated its ability to deliver rhBMP-2 for the repair of critically-sized segmental bone defects in vivo. For control group comparisons, we also examined the ability of the nanofiber mesh alone, and in combination with alginate hydrogel, to heal the bone defects without rhBMP-2. Finally, the effect of a perforated nanofiber mesh design on bone repair was investigated.

Materials and Methods

Fabrication of nanofiber mesh tubes. Poly (ε-caprolactone) (PCL) pellets (Sigma-Aldrich, St. Louis, Mo.) were dissolved in a 90:10 volume ratio of hexafluoro-2-propanol (HFP):dimethylformamide (DMF) (Sigma-Aldrich) to obtain a 12% (w/v) polymer solution. DMF was first slowly added to HFP to prevent excessive heat generation, and mixed well on a stir plate for 5 minutes. The PCL pellets were then added to the solvent solution, and gently stirred for 16-24 hours. The solution was visually inspected to ensure a homogeneous and clear solution. The polymer solution was loaded in a 3 mL syringe (Becton-Dickinson, Franklin Lakes, N.J.), and a 22 gauge blunt stainless steel needle (Jensen Global Inc., Santa Barbara, Calif.) was attached to the syringe end. The syringe was mounted on a syringe pump (Harvard Apparatus, Holliston, Mass.) set at a rate of 0.75 mL/hr. The fibers were collected on a flat copper plate (McMaster-Carr, Atlanta, Ga.) which was placed at a distance of 20-23 cm from the needle end. Fibers were electrospun for 5 hours at a voltage of 13-20 kV, supplied by a high voltage power supply (Gamma High Voltage Research, Ormond Beach, Fla.), to obtain a thick sheet of nanofiber mesh. The residual solvent from the meshes was allowed to evaporate by placing them in a dessicator overnight. The morphology of the nanofiber meshes was examined using a Scanning Electron Microscope (SEM; Hitachi HTA, Pleasanton, Calif.) after gold coating using a sputter coater (Quorum Technologies, East Granby, Conn.). The diameter of the fibers were quantified by analyzing the SEM images (at 7000 magnification) using a custom MATLAB® (The MathWorks Inc., Natick, Mass.) code.

The nanofiber meshes, as fabricated above, were used to create tubular implants. Rectangular samples measuring 13×19 mm were cut from a mesh. In some samples, perforations spaced approximately 1.5 mm apart were made in the mesh using a 1 mm diameter biopsy punch (Miltex Inc., York, Pa.). The rectangular mesh samples were wrapped around a steel mandrel (McMaster-Carr) to form a tube having a diameter of approximately 5 mm and 13 mm length. The overlapping edges of the mesh were secured together by using UV glue (DYMAX Corporation, Torrington, Conn.), which was cured with a LED spot curing lamp (DYMAX Corporation). The nanofiber mesh tubes were then rinsed twice in 70% alcohol (VWR, West Chester, Pa.), and sterilized by submerging in 200 proof ethanol (Sigma-Aldrich) and allowing the ethanol to evaporate overnight. After the samples had dried completely, they were pre-wetted with sterile 70% ethanol for 30 minutes. After aspirating the 70% ethanol, the mesh tubes were rinsed three times with excess phosphate-buffered saline (PBS; Mediatech Inc., Manassas, Va.), and placed in aMEM (Invitrogen) until implantation.

Preparation of Alginate Hydrogel with and without Growth Factors. Briefly, Irradiated RGD-modified alginates were prepared by subjecting MVG sodium alginate (FMC Biopolymer) to a 5 Mrad dose of gamma irradiation. This reduces the molecular weight of the polymer leading to a faster degradation rate, which makes it more appropriate for in vivo studies. The irradiated alginates were then covalently coupled with $G_4$RGDASSP peptide sequences (Commonwealth Biotechnologies, Richmond, Va.) at a density of 2 sequences per polymer chain using standard carbodiimide chemistry. The resulting RGD-alginates were sterile filtered, lyophilized and stored at −20° C.

To prepare hydrogels, the RGD-alginates were reconstituted in α-MEM to obtain a 2.5% (w/v) solution. Lyophilized rhBMP-2 (R&D Systems, Minneapolis, Minn.) was reconstituted in 0.1% rat serum albumin (RSA; Sigma-Aldrich) made in 4 mM HCl, at a concentration of 200-μg/mL. The alginate solution was then mixed with either the rhBMP-2 solution at a ratio 5:1 (700-μL alginate solution @2.5% (w/v) with 175-μL rhBMP-2 @200-μg/mL or 0.1% RSA). This results in a 2% (w/v) alginate solution containing 40-μg/mL rhBMP-2. The rhBMP-2 containing alginate solution was cross-linked with a calcium sulfate (Sigma-Aldrich) slurry (0.21 g $CaSO_4$ per 1 mL deionized water) at a ratio of 25:1 (35 μL of $CaSO_4$ with 875 μL of alginate/rhBMP-2 solution). The mixing was performed in two 1-mL syringes (Becton-Dickinson, Franklin Lakes, N.J.) coupled with a syringe connector (Cole-Parmer, Vernon Hills, Ill.) with Luer-Lok fittings to minimize air bubbles. Another set of hydrogels was prepared without rhBMP-2 by substituting the rhBMP-2 solution with the carrier (0.1% RSA) alone. The alginate solutions were allowed to gel in the syringes for 30 minutes at room temperature and then transferred to 4° C. The hydrogels were kept at 4° C. overnight and used in surgery the following day. Aseptic conditions were maintained in all the above steps, including handling of the exterior of the syringe.

rhBMP-2 release kinetics. RGD-alginate solutions containing rhBMP-2 were cross-linked with a calcium sulfate slurry as above, and immediately injected into custom designed molds containing 4 mm diameter wells. The alginate solutions were allowed to gel for 30 minutes at room temperature, producing cylindrical plugs measuring 4 mm in diameter and 8 mm in length. Each cylindrical alginate plug contained 500-ng rhBMP-2. Following a brief rinse in 0.1 M $CaCl_2$ (Sigma-Aldrich), the samples were incubated at 37° C. in 1-mL PBS containing calcium and magnesium ions. At specific time points through day 21, the entire buffer solution was collected and replaced with fresh 1-mL PBS. On days 0 and 21, alginate plugs were dissolved by immersing in 8-mL and 2-mL, respectively, of 2% (w/v) sodium citrate (Sigma-Aldrich) for 30 minutes at room temperature. The amount of rhBMP-2 present in the collected PBS and sodium citrate solution was quantified using an ELISA kit (R&D Systems), following the manufacturer's instruction.

Surgical procedure and analysis. An established critically-sized, femoral segmental defect rat model was used in this study. All surgical procedures were approved by the Institutional Animal Care and Use Committee (IACUC protocol #A05041) at the Georgia Institute of Technology. The rat model and surgical technique has been described previously. Briefly, bilateral 8 mm segmental defects were created in the mid femoral diaphyses of 13-week old female Sasco Sprague-Dawley rats. Prior to defect creation, the femora were stabilized by modular fixation plates consisting of a polysulfone plate and two stainless steel plates. This is a more challenging segmental defect model compared to the 5-6 mm defect models that are used most frequently in the field. Nanofiber mesh tubes were placed around the adjacent bone ends such that the tube lumen contained the defect and there was an overlap of 2.5 mm with the native bone ends at each end of the tube. In some groups, 125-μL pre-gelled 2% alginate with or without 5-μg rhBMP-2 was injected in the tube lumen using a 22 g needle (Jensen Global Inc.). As it is a soft hydrogel, the pre-gelled alginate is ejected from the needle in a continuous thin filament shape and fits compactly inside the tube. The tubes used for one of the groups had 1 mm diameter perforations to enhance vascular invasion during the repair process. The four groups (n=6-8) were as follows: (I) Mesh alone, (II) Mesh with alginate, (III) Mesh with alginate containing rhBMP-2, (IV) Table 1 provide the four groups utilized in the in vivo study, with the implant conditions in each group.

Perforated mesh with alginate containing rhBMP-2. The groups were assigned to the right and left limbs to evenly distribute pairs of groups and obtain a balanced experimental design. After surgery, the animals were allowed to recover and move freely. For pain relief, the animals were injected with 0.03 mg/kg buprenorphine subcutaneously every 8 hours for the first 48 hours and 0.01 mg/kg buprenorphine for the next 24 hours. Radiographs and in vivo micro-computed tomography (μCT) images were obtained at 4 and 12 weeks after surgery to evaluate bone healing. The rats were euthanized at 12 weeks and femora were extracted for mechanical testing. Histological analysis was performed on femora extracted at 4 and 12 weeks.

TABLE 1

| Group # | Nanofiber mesh tube | Perforations | Alginate | rhBMP-2 |
|---|---|---|---|---|
| I | + | − | − | − |
| II | + | − | + | − |
| III | + | − | + | + |
| IV | + | + | + | + |

2-D radiographs and 3-D in vivo μCT imaging. At 4 and 12 weeks after implantation, two-dimensional radiographs (Faxitron MX-20 Digital, Faxitron X-ray Corp., Wheeling, Ill.) of the femur were taken to qualitatively assess bone regeneration and defect bridging. For the quantitative evaluation of bone formation, in vivo μCT was performed at the same time points. The rats were anesthetized by isoflurane and placed in an in vivo μCT system (Viva-CT, Scanco Medical, Bassersdorf, Switzerland). The femoral defect region was scanned at a 38.5-μm voxel resolution, a voltage of 55-kVp and a current of 109-p A. The radiotranslucent polysulfone plate does not interfere with μCT scanning and therefore allows longitudinal evaluation of bone ingrowth.

To obtain a consistent volume of interest (VOI) between animals and to avoid including the native bone ends, only the central 4 mm of the 8 mm defect was analyzed in vivo by drawing circular contours. A Gaussian filter (sigma=1.2, support=1) was used to suppress noise in the VOI, and a global threshold corresponding to a density of 270.3 mg hydroxyapatite/cm$^3$ was applied to obtain the regenerated bone volume. This threshold was selected by the visual inspection of individual scan slices to detect newly formed bone and to exclude soft tissues, the polysulfone fixation plate and the nanofiber mesh tube. The volume and density of the segmented bone was noted. In addition, the density map was calculated in the segmented bone volume, and presented as a pseudo color-scaled image.

Torsional testing. The freshly extracted femora at 12 weeks were wrapped in gauze moistened with PBS, and stored at −20° C. Just before testing, samples were thawed in PBS and the majority of soft tissues adjacent to the bone removed. The ends of the femur were embedded in end blocks using Wood's metal (Alfa Aesar, Wood Hill, Mass.) and aligned using a custom fixture. The polysulfone plate was then detached from the metal plates to enable loading of the bone. The potted femur was loaded into holding brackets mounted on a Bose ElectroForce system (ELF 3200, Bose EnduraTEC, Minnetonka, Minn.) fitted with a 2 Nm torsional load cell. The samples were rotated to failure at a rate of 3° per second under displacement control, and the torque and rotation were recorded. Maximum torque was calculated by locating the failure torque, which occurred within the first 15° for bridged defects. Samples that did not bridge displayed a gradual increase in torque and the absence of a sharp failure point, due to soft tissue stretching. For these samples, the failure torque was measured in the first 60° to avoid analyzing the forces generated due to the stretching of soft tissues. Stiffness was calculated by finding the slope of the straight line fitted to the linear portion of the torque-rotation plot before failure.

Histological analysis. One representative sample from each group was selected for histological evaluation at 4 and 12 weeks. The extracted femora were fixed in 10% neutral-buffered formalin for 48 hours. They were dehydrated in a series of alcohol solutions of increasing concentrations, infiltrated with methyl methacrylate (MMA), and embedded by polymerizing the MMA. Ground sections, 50-80 µm thick, were generated using a EXAKT Grinding System (EXAKT Technologies, Oklahoma City, Okla.). The sections were stained with Sanderson's Rapid Bone Stain and a van Gieson counter stain (SURGIPATH Medical Inc., Richmond, Va., USA). This stain permits the detection of bone (pink), muscle (blue green) and cells (blue).

Analysis of vascularity during bone regeneration. The vascular regrowth at the defect area was investigated at 3 weeks post-surgery by using a modified version of the µCT-based angiography technique developed in our laboratory. After induction of anesthesia using isoflurane, a 25 gauge catheter was introduced into the abdominal aorta and 250 units (0.25 mL of 1000 units/mL) heparin were injected. The rat hind limb vasculature was cleared with PBS, fixed with 10% neutral buffered formalin and cleared again with PBS using a peristaltic pump (Masterflex, Cole-Parmer). The rats were euthanized by an overdose of isoflurane before the formalin perfusion. A radiopaque, lead chromate based contrast agent (Flow Tech, Carver, Mass.) was then injected and allowed to polymerize for at least two hours. The femur along with its musculature was excised carefully, fixed in 10% neutral buffered formalin for 48 hours, and decalcified for 2 weeks using a formic acid based solution (Cal-Ex II, Fisher Scientific). The samples were rinsed in PBS and stored in 10% neutral buffered formalin until imaging. They were imaged in a µCT system (Viva-CT, Scanco Medical) at a 21.5-µm voxel size. Two VOIs were defined to analyze the vessels inside the defect and adjacent to the defect. The images were globally thresholded based on X-ray attenuation to segment the contrast-filled vasculature from surrounding tissues.

Statistical analysis. Data were analyzed by analysis of variance (ANOVA) conducted in Minitab® 15 (Minitab Inc., State College, Pa.). Pairwise comparisons were made using the Tukey multiple comparison procedure. The normality of the residuals was evaluated by the Anderson-Darling normality test. To detect the presence of any pattern in the residual distribution, they were plotted against fitted values. To maintain the constancy of error variance and normality of error terms, data were transformed according to the Box-Cox procedure, wherever required. To investigate the effect of time on sequential in vivo µCT data, paired t-tests were performed. A p-value<0.05 was considered statistically significant. All data are shown as mean±standard error of mean (SEM).

Results

Nanofiber mesh tube characterization and placement. The nanofibers obtained by electrospinning were observed to be smooth and bead-free (FIG. 21A). The fibers ranged in diameter from 51 nm to 974 nm with 82% of the fibers between 50 nm and 150 nm. The mean and the median fiber diameter were found to be 154 nm and 107 nm respectively. After 5 hours of electrospinning, the mesh was found to be approximately 300-400 µm thick. This thickness was sufficient to provide a bending stiffness that prevented collapse of the mesh in solution. The thick nanofiber meshes were able to be wrapped tightly around a steel mandrel, and glued to form a tube (FIGS. 21B and C). Due to the fast curing time of the UV glue, it was localized to the overlapping edges and did not seep to the rest of the mesh. The perforated meshes held the tubular structure well, and the holes accounted for 10% of the total surface area of the mesh tube. The nanofiber mesh tubes were deformed slightly to place them around the native bone ends of the segmental defect, but they regained their original shape due to the elasticity of the mesh. The overlapping ends and the surrounding musculature resulted in the tubes being stably located around the defect for the duration of the study (FIGS. 21D and E). In some samples that were taken down after one week, the alginate was found to be still present inside the tube lumen, even in perforated tubes, with hematoma formation at the bone ends (FIG. 21F).

Alginate release kinetics. The in vitro release of rhMBP-2 from alginate hydrogel plugs was monitored over a period of 21 days (FIG. 21G). After dissolving the alginate plugs on day 0, 275.5±15.6 ng rhBMP-2 was detected in the resulting solution, indicating that the functional encapsulation percentage was 55.1%. Of the amount encapsulated, 25.8% (71.2±3.8 ng) was released in the buffer solution in active form by day 21. The majority of the release took place within the first 7 days (98.6% of total released). The amount of rhBMP-2 retained in the gels was also assayed by dissolving them at day 21, and found that 9.9% (27.2±3.3 ng) of the encapsulated amount was still present in the gels. It is possible that the binding of some of the rhBMP-2 molecules to the alginate fibers masks the antibody binding site. This subset of rhBMP-2 molecules would not be detected by the ELISA, and therefore the actual amount of rhBMP-2 present in the hydrogels may be higher.

Figure 22:
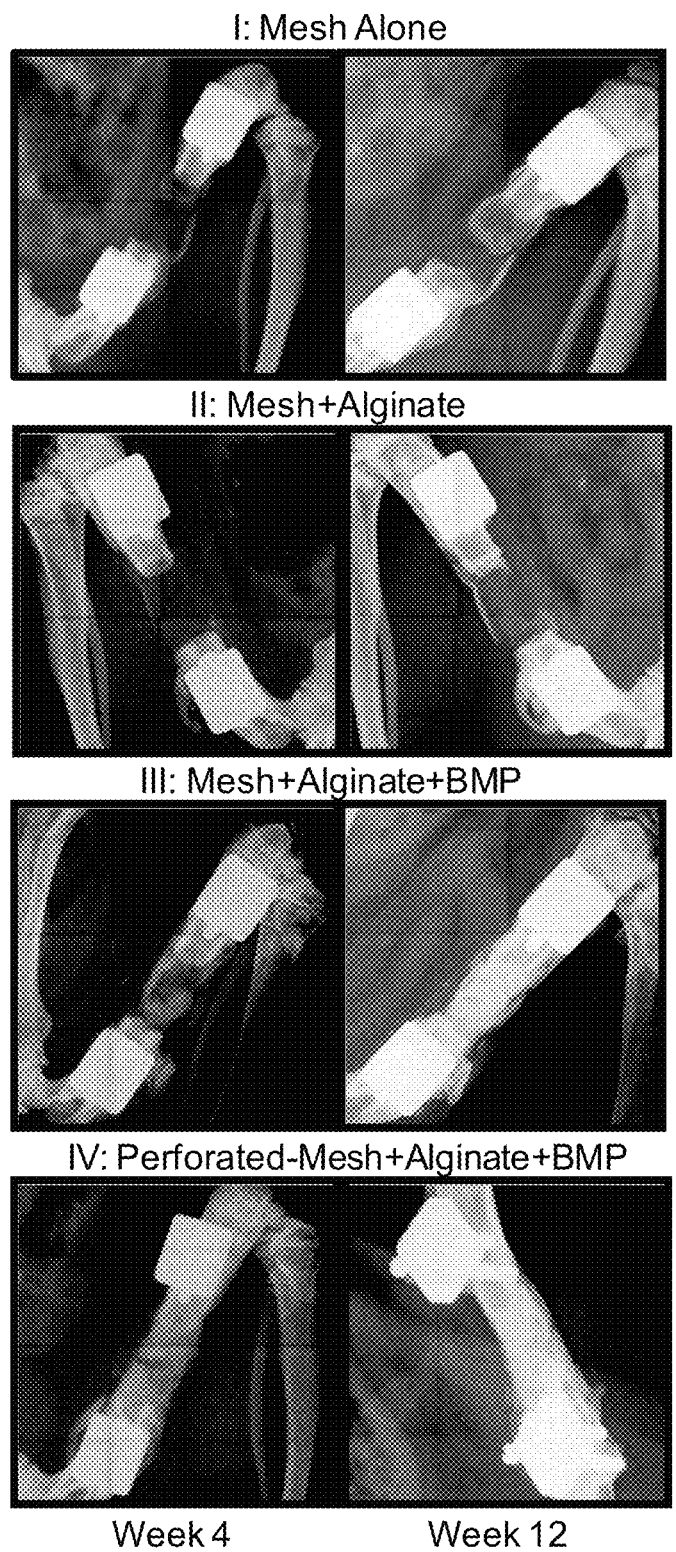
FIG. 22 provides representative radiographs at 4 and 12 weeks.

Radiographs. Two-dimensional radiographs were taken at 4 and 12 weeks for qualitative assessment of bone healing (FIG. 22). Radiographs at the early time point of 4 weeks indicated that Groups I & II (Table 1) specimens had small amounts of bone formation, originating from the cut native ends and extending somewhat along the periphery. Group I samples were implanted with a nanofiber mesh tube alone, whereas Group II contained, in addition, alginate hydrogel inside the mesh tube. On the other hand, samples from Groups III and IV, in which 5-μg rhBMP-2 was delivered within alginate, demonstrated significant infiltration of mineralized tissue throughout the defect. Group IV specimens that were implanted with the perforated mesh tube exhibited the most robust mineralization. Group IV demonstrated the highest bridging rate (5/8) at the 4 week time point, whereas the remaining 3/8 defects were nearly bridged. Group III had none bridged, but 3/6 defects were nearly bridged. At 12 weeks, Groups I and II had still not achieved osseous union in any specimen, with most of the bony tissue formed on the periphery. In contrast, all specimens in Groups III and IV were completely bridged with densely packed bone.

In vivo μCT imaging. Animals were scanned in an in vivo μCT system at 4 and 12 weeks for quantifying bone formation (FIGS. 23A-C). The three-dimensional μCT images revealed that new bone formation in Groups III and IV occurred throughout the cross-section of the defect, whereas it appeared predominantly at the native bone margins and the periphery in Groups I and II (FIG. 23A). The analysis of regenerated bone volumes indicated that Groups III and IV (Table 1) had significantly more (a; $p<0.05$) bone formation in the defect compared to Groups I and II, at both time points (FIG. 23B). At 4 weeks, Group IV, implanted with the perforated mesh, had significantly more (b; $p<0.05$) bone formation than Group III, which contained the mesh tubes without holes. However at 12 weeks, there was no difference in bone volumes between Groups III and IV. There was a significant increase in bone volumes with time in Groups I ($p=0.048$), III ($p<0.001$) and IV ($p=0.001$), but not in Group II ($p=0.08$). Group III ($37.65\pm2.22$ mm$^3$) samples demonstrated the greatest increase in bone volume between 4 and 12 weeks, followed by Group IV ($20.02\pm2.96$ mm$^3$) Compared to these two groups, Groups I ($3.96\pm1.40$ mm$^3$) and II ($2.09\pm0.80$ mm$^3$) had significantly less bone accumulation during the same period.

The density of the newly formed bone within the defect was also calculated at 4 and 12 weeks (FIG. 23C). At 4 weeks, Groups I and II contained higher density bone than Groups III and IV (b and c respectively; $p<0.05$). Group IV samples demonstrated a density higher than Group III, at both 4 and 12 weeks (b; $p<0.05$). There was a significant increase in density with time for all groups from 4 to 12 weeks.

Biomechanical properties. Torsional testing was performed on extracted femora at 12 weeks to test their biomechanical properties (FIG. 24). Age-matched non-operated femora were also tested to obtain properties of native intact bone. The maximum torque and stiffness in torsion was calculated from the torque-rotation data. Groups III and IV had significantly higher (a; $p<0.01$) maximum torque and stiffness compared to Groups I and II, as did the intact bone. There was no significant difference between Groups III and IV. However, compared to the intact bone, only Group IV samples had statistically equivalent maximum torque and stiffness, whereas Group III samples had significantly lower properties (b; $p<0.05$). The mechanical properties for Group IV were on average approximately 75% of those for intact bone.

Histological analysis. Ground MMA sections were stained and analyzed for examining the regenerated tissue (FIGS. 25A and B). The nanofiber mesh tube was partially degraded due to the MMA processing steps, but is still seen to be located around the defect. In Groups I and II, very little mineralized tissue was observed in the defect site at 12 weeks, similar to the radiographic and μCT results (FIG. 25A: I and II). The defects in these specimens were sparsely populated with fibrous tissue. The new bone formation was limited to the proximity of native bone ends and along the mesh tube. The end of the defects remained disconnected, with the capping of the native ends with bony tissue. The sections from Groups III and IV revealed extensive mineral deposition and bony bridging of the defects in these groups (FIG. 25A: III and IV). The newly formed bone was observed to be a combination of immature woven bone and mature lamellar bone. There was good continuity of the newly mineralized matrix with the native bone ends. Group IV, in particular, demonstrated the presence of a higher amount of lamellar bone, better integration at the native bone interface and development of marrow-like tissue. The dark areas correspond to undegraded alginate and the partially degraded mesh. The higher magnification images of Groups III and IV indicated the presence of osteocytes embedded in lacunae and osteoblasts lining the new bone surfaces (FIG. 25B). Histological analysis performed at 4 weeks revealed no evidence of cartilage tissue formation or endochondral ossification, indicating direct, intramembranous bone formation within the alginate gel (data not shown). The density maps obtained from the μCT indicate good correlation with histology sections (data not shown). In addition, Group IV appeared to contain higher density mineralized tissue, which was distributed in a tubular pattern, similar to that of native cortical structure.

μCT-based angiography. Animals implanted with the rhBMP-2 containing Groups III and IV were euthanized at 3 weeks post-implantation, and their hind limb vasculature perfused with a radiopaque contrast agent. The femur and the surrounding soft tissues were imaged using μCT to quantify vascular ingrowth at an early time point preceding bone regeneration. Contours were drawn to define two VOIs. The first VOI included only the volume inside the defect region, whereas the second contained both the defect and the periphery of the defect, termed the total VOI (FIG. 26). The analysis of the vasculature revealed the presence of vessels, both inside and outside the defect. The majority of the vascularity was observed in the periphery, as indicated by the significantly larger vessel volume in the total VOI (a; $p<0.001$). There were no significant differences in vascular volume between Groups III and IV, in either the defect or the total VOI.

This Example demonstrates a novel growth factor delivery technique for the functional repair of large bone defects using an electrospun nanofiber mesh tube and alginate hydrogel. Tubular scaffolds constructed from nanofiber meshes were placed around segmental defects. Alginate hydrogel containing 5-μg rhBMP-2 was injected into the tubes and constrained within the defect site by the mesh tube. The above results demonstrate that this technique results in substantial bone formation and complete defect bridging. Samples implanted with both perforated mesh tube and rhBMP-2 containing alginate had statistically equivalent biomechanical properties to those of intact age-matched femora, indicating functional restoration of the limb function.

The majority of scaffolds proposed for bone reconstruction are structural scaffolds designed to support in vivo loads and provide a three-dimensional framework for cell attachment. They are examples of "hard scaffolds", usually made from slowly hydrolyzing polymers or ceramics with unpredictable degradation. Though they provide a structure for tissue growth, it is difficult to fine-tune their degradation rate to match the rate of tissue formation. The use of structural scaffolds also precludes the use of the intramedullary pin for limb fixation, a technique frequently used by orthopedic surgeons. In addition, the regular geometric shape of these scaffolds made them unsuitable to be placed inside fractures, which usually have irregular edges. Thin scaffold membranes have also been used for bone repair in a procedure termed guided bone/tissue regeneration. In this technique, the membranes are positioned on the periosteal surface to provide a structure for bone formation. It has been argued that while 3-D scaffolds support the ingrowth of cells and tissue, the 2-D membranes may also protect the defect from soft tissue ingrowth and guide cell migration from the periosteum. Since the membranes are placed on the periphery of the defect, they retain space for bone deposition throughout the defect. However, when a large mass of bone is lost, repopulating the entire defect with cells would be a challenge due to the presence of a large void.

Hydrogels are a class of highly hydrated materials that enable cellular and tissue infiltration with relative ease. Alginate hydrogels are an example of such a "soft scaffold" that can deployed using minimally invasive procedures, conform to the shape of the defect and be manipulated by cells during tissue regeneration. In addition, they can be used for sustained delivery of osteoinductive growth factors, a typical requirement for healing large defects. The primary concern with hydrogels is their inadequate mechanical stiffness, which causes them to deform easily under load.

Discussion. In this Example, we present a novel hybrid technique that utilizes both a nanofiber mesh membrane and an alginate hydrogel. The mesh tubes prevent soft tissue invagination into the defect and create a space for tissue regeneration. In addition, they potentially guide the migration of progenitor cells along the periosteal surface, and retain the osteogenic factors within the defect site. However, nanofiber mesh tubes, alone or in presence of alginate hydrogel without rhBMP-2, were not sufficient to bridge the 8 mm segmental defects in rat femora. Without the presence of the osteoinductive protein, the center was only sparsely populated by cells and bony tissue capped the ends of the defect.

The above results illustrate higher bone formation with the sustained release of rhBMP-2 from the alginate hydrogel. All defects in the rhBMP-2 groups (Groups III and IV) were bridged by 12 weeks with densely packed, cell mediated mineralized tissue. This suggests that the release of rhBMP-2 is able to attract osteoprogenitor cells into the defect from the adjacent periosteum, marrow and vascularized tissues, and induce them to undergo osteogenic differentiation. The release of proteins from alginate occurs due to a combination of diffusion and gel degradation. It is interesting to note that after 21 days, at least 10% of the functionally encapsulated rhBMP-2 was still present in the alginate, though the amount of the protein released at this time point was negligible. This suggests that a portion of the protein binds to the alginate polymer, which at later time points may be available to the invading cells.

The presence of perforations in nanofiber mesh tubes accelerated early bone formation and defect bridging. The utilization of in vivo μCT scanning techniques permitted the sequential scanning of animals at multiple time points, and revealed that perforations in mesh tubes enhanced bone formation at 4 weeks. However, by 12 weeks, the group without perforations (Group III) had comparable bone volume to the group with perforations (Group IV). The differences in the bone deposition rate between 4-12 weeks could be attributed to the fact that at week 4, Group IV defects were almost filled with newly formed bone, whereas Group III defects still exhibited substantial space for bone formation. Compared to Group III, the density of the newly formed bone was significantly higher in Group IV. Also, only Group IV femora demonstrated functional restoration of biomechanical properties. These results indicate that perforations in the nanofiber mesh tube expedited bone formation, resulting in advanced bone remodeling and improved mechanical properties.

There are two potential mechanisms that mediate the acceleration of bone formation due to perforations in our hybrid delivery system. The perforations may enhance invasion of vascularity or improve osteoprogenitor cell migration from the surrounding soft tissues into the defect region. We initially hypothesized that perforations improve vascular invasion, and employed a μCT-based technique to quantitatively assess the vascularity in the early stages of bone regeneration. However, our results indicated that the perforations did not have a significant effect on vascularity at the defect site. In addition, it was seen that only a fraction of the total vessels were present inside the defect. It is possible that the scan resolution was too low to detect the microvasculature in the developing bone. The lack of differences in vascular regrowth due to the perforations suggests that the acceleration of bone formation was due to improved osteoprogenitor cell migration into the defect.

The current clinical technique for rhBMP-2 delivery involves soaking a collagen sponge with rhBMP-2 solution, which primarily relies on the adsorption of the protein to collagen. Numerous sustained delivery systems are being currently developed from natural and synthetic materials for reducing the high rhBMP-2 dose required clinically. By providing a sustained and localized release of rhBMP-2 and permitting robust cell infiltration, the hybrid alginate/nanofiber mesh system creates an environment conducive for bone regeneration. The 5-μg dose utilized in this study is in the lower range of what has been reported (2-20 μg) in similar models. For example, in a 8 mm rat segmental defect model, 20-μg of rhBMP-2 delivered on inactive demineralized bone matrix was required for defect bridging.

In conclusion, a novel hybrid growth factor delivery system was presented in this Example. This system resulted in complete bony bridging of challenging segmental bone defects in a rat model. Perforations accelerated the deposition of mineralized tissue, and resulted in functional repair, by perhaps improving osteoprogenitor cell migration into the defect. The mesh tube alone, or in combination with alginate hydrogel, did not generate a strong repair response. The sustained delivery of rhBMP-2 via alginate hydrogel was required for substantial regeneration to occur. These results indicate that this hybrid technique may be clinically useful for bone regeneration in the case of fracture non-unions and large bone defects.

Example 4

Delivery of Bone Morphogenetic Protein within Nanofiber Mesh/Alginate Enhances Segmental Bone Defect Repair The purpose of this study was to compare the hybrid nanofiber mesh/alginate BMP delivery technique with the clinical standard of BMP delivery on collagen matrix. In addition, the role of the nanofiber mesh tube as a spatial constraint was investigated. Our hypotheses were that BMP delivery within alginate hydrogel would enhance bone formation, and that the mesh tube would aid in the spatial retention of the regenerated bone. To test this hypothesis, we evaluated the structural and biomechanical properties of the regenerated bone in a challenging rat segmental defect model.

Materials and Methods

Nanofiber mesh tube fabrication and alginate preparation. Nanofiber meshes were made by electrospinning and formed into tubes as described in Example 4. Briefly, a 12% (w/v) solution of poly (ε-caprolactone) (PCL) was made by dissolving the polymer in a 90:10 volume ratio of hexafluoro-2-propanol:dimethylformamide. The following parameters were used during electrospinning: flow rate: 0.75 mL/hr; voltage: 13 kV; collector distance: 17 cm; needle gauge: 22. Fibers were collected for 6 hours to obtain nanofiber meshes having a thickness of approximately 300-400 μm. Perforations measuring 1 mm in diameter and spaced approximately 1.5 mm apart were made in rectangular 13×19 mm mesh samples using a biopsy punch. The mesh samples were wrapped around a steel mandrel and glued using UV glue (DYMAX Corporation, Torrington, Conn.) to form hollow tubular implants having a diameter of approximately 5 mm and 13 mm length.

Medical grade alginate, MVG (FMC Biopolymer, Philadelphia, Pa.), was irradiated with a 5 Mrad dose of Gamma irradiation, and covalently coupled with RGD-containing G4RGDAS SP peptide sequences. Alginate hydrogels, encapsulating 33.33 μg/mL rhBMP-2, were prepared in 1 mL syringes at a concentration of 2% (w/v) by crosslinking the alginate with calcium sulfate slurry (Chapter 5). For one of the experimental groups, the hydrogels were made in the form of cylindrical plugs (φ5 mm; 9 mm length) by using a custom built mold.

Animal model and bone regeneration analysis. Femora of 13 week old female Sasco Sprague-Dawley rats were stabilized with custom fixation plates. Bilateral 8 mm segmental defects were created in the mid femoral diaphyses with an oscillating saw under irrigation. A 5 μg dose of rhBMP-2 was delivered to each defect in one of three different ways shown in Table 2. In Group I, a collagen scaffold (φ5 mm; 9 mm length) was soaked with 150 μL of 33.33 μg/mL rhMBP-2 solution for 15 minutes, and implanted in the defect. The collagen scaffolds were obtained from a fibrous collagen sheet (average pore size 61.7 μm, 93.7% pore volume, Kensey Nash, Exton, Pa.). Group II implants consisted of a cylindrical scaffold (φ5 mm; 9 mm length) made from alginate containing 5 μg rhBMP-2. In Group III, perforated nanofiber mesh tubes were placed around the defect, and injected with 5 μg rhBMP-2-containing alginate using a 22 g needle.

Radiographs and μCT images of 8-10 samples per group were obtained at 4 and 12 weeks to assess bone formation. Radiographs were also taken at 2 weeks to assess early differences between groups. In addition to the volume of newly formed bone at each time point, μCT data was processed to obtain mean density, connectivity density and temporal changes in volume of the regenerated bone. Based on the two dimensional scan slices, an appropriate threshold was selected at each time point to detect new bone formation.

Torsional testing was performed on extracted femurs at 12 weeks using a Bose ElectroForce system (ELF 3200, Bose EnduraTEC, Minnetonka, Minn.) to test their biomechanical properties. Maximum torque and failure angle were measured at the failure point from the torque-rotation data, and the work to failure was calculated using these values. Torsional stiffness was calculated by fitting a straight line to the linear portion of the curve before failure. Histological analysis was also performed at 12 weeks by embedding decalcified femurs in glycol methacrylate (GMA) and staining 5 μm sections with H&E.

Data analysis. Data are presented as mean±standard error of mean (SEM). Data were analyzed using ANOVA and Tukey's tests for pairwise comparisons (significance set at p<0.05). When data were not normal, the nonparametric Mann-Whitney test was used to compare between groups. Minitab 15 (Minitab Inc., State College, Pa.) was used for all statistical analysis.

TABLE 2

| Group | Description |
| --- | --- |
| Group I | Collagen scaffold + 5 μg rhBMP-2 |
| Group II | Alginate scaffold + 5 μg rhBMP-2 |
| Group III | Perforated nanofiber mesh tube + Alginate + 5 μg rhBMP-2 |

Results

Figure 27:
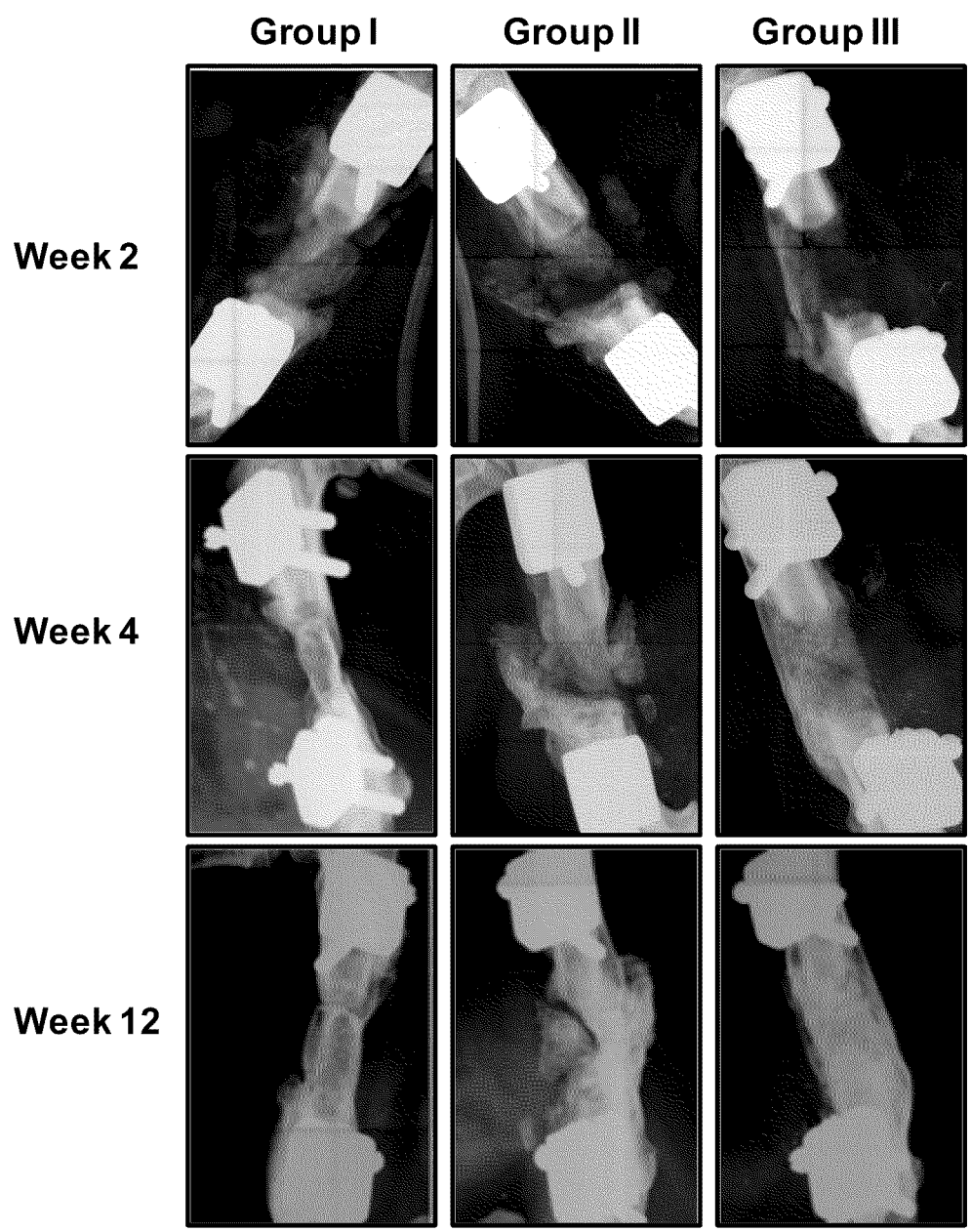
FIG. 27 displays representative radiographs at 2, 4 and 12 weeks.
Figure 28:
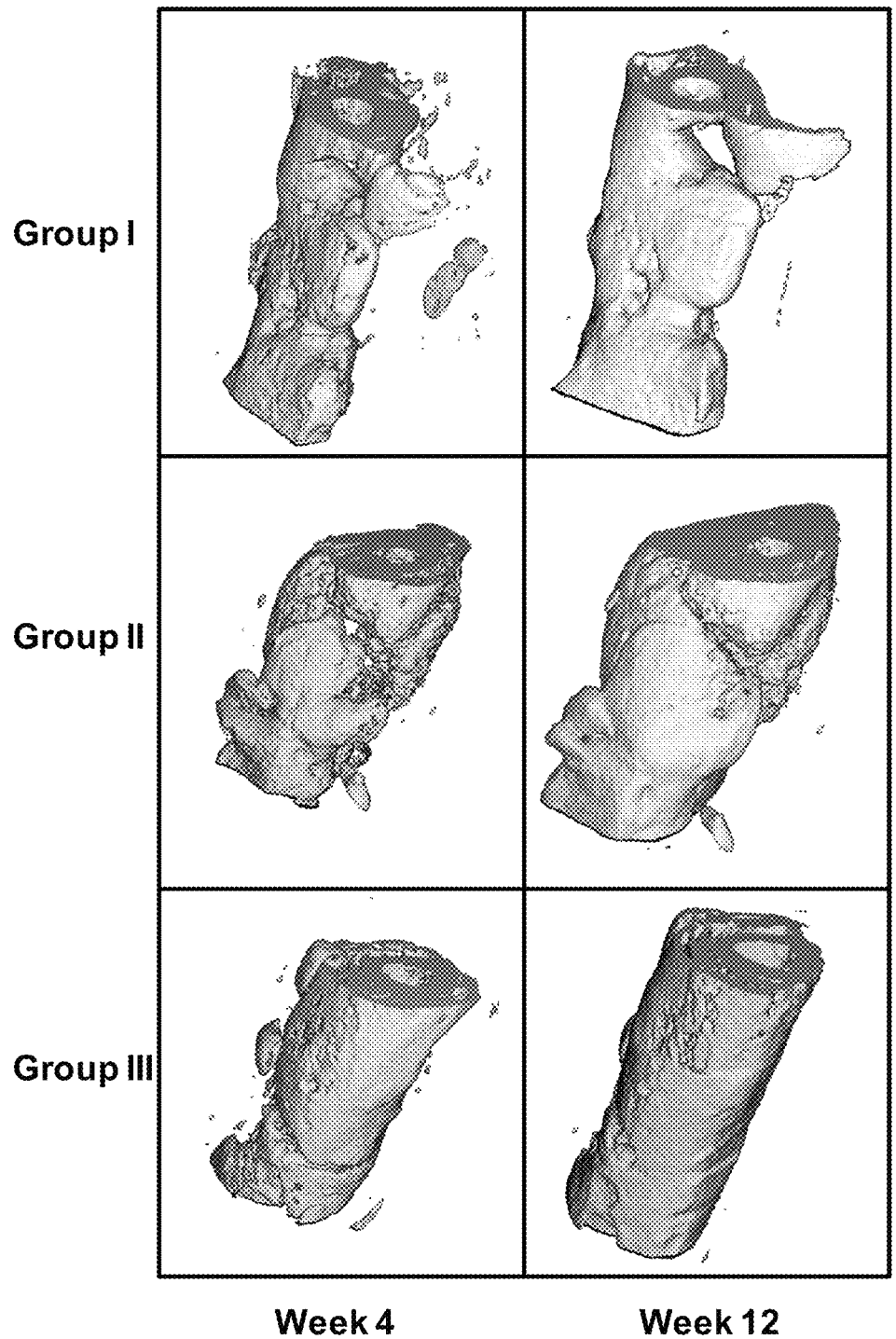
FIG. 28 illustrates three-dimensional in vivo μCT images at 4 and 12 weeks.

Radiographs. The radiographs at the early time point of 2 weeks illustrated that, while considerable new bone deposition was evident in the collagen scaffold group (Group I), the alginate groups (Groups II and III) demonstrated comparatively less bone formation (FIG. 27). In contrast, the radiographs at 4 and 12 weeks revealed that the alginate groups exhibited higher amount of bone, though there was substantial bone regeneration in all groups at 4 weeks and bridging of all defects after 12 weeks. In addition, there were differences in the distribution and density of bone deposition among groups. Group I samples appeared to have more trabecular-like bone that was not as densely packed as the other two groups. Group II demonstrated mineral deposition both within and outside the defect, suggesting some alginate scaffold displacement or protein diffusion. In contrast, samples in Group III exhibited consistent localization of dense new bone formation inside the defect.

μCT analysis. The three-dimensional μCT images obtained in vivo at 4 and 12 weeks were consistent with the radiographs (FIG. 28). The collagen scaffold group (Group I) demonstrated substantial bone formation in the defects by 4 weeks. Specimens in the alginate scaffold group (Group II) exhibited a fragmented distribution of mineralized tissue, with substantial bone formation occurring outside the defect region. In contrast, in the presence of a nanofiber mesh tube (Group III), new bone formation was confined within the defect region and displayed a continuous distribution.

μCT analysis determined that the amount and distribution of regenerated bone was significantly affected by the rhBMP-2 delivery method. Two volumes of interest (VOI) were defined for the quantitative analysis of bone distribution. The central VOI corresponds to an interior cylindrical volume that captures the defect. The total VOI contains the entire volume of mineralization, in and around the defect, including the irregular bone formation outside the defect. At both 4 and 12 weeks, the alginate delivery groups (Groups II and III) had significantly more bone formation than the collagen delivery groups (Group I) (FIG. 29A). The bone volume in the central VOI at 4 weeks was not significantly higher in Group II compared to Group I; however the p value was very close to significance (p=0.051). Although there was no difference between Groups II and III at 4 weeks, the central VOI analysis at 12 weeks revealed a significant increase in bone formation within the defect region associated with use of the nanofiber mesh tube (Group III). However, it was observed that the total bone volume at 12 weeks was not significantly different between Groups II and III. The change in bone volume between 4 and 12 weeks was calculated for each specimen (FIG. 29B). This analysis demonstrated that Group III specimens had the largest increase in mineral accumulation between the two time points.

Mean density and connectivity density of the newly formed bone were evaluated at 4 and 12 weeks (FIG. 30). The results indicate that the mean bone density in Group III specimens was significantly lower than those in Groups I and II, at both time points and in both VOIs. There was more than a 50% increase in the density of all groups between 4 and 12 weeks, indicating maturation of the mineralized tissue. At 4 weeks, the connectivity density in Group III was significantly higher than the other two groups, though there were no differences at 12 weeks. Finally, it was observed that the newly formed bone in the central VOI displayed higher connectivity density than that contained in the total VOI.

Figure 31:
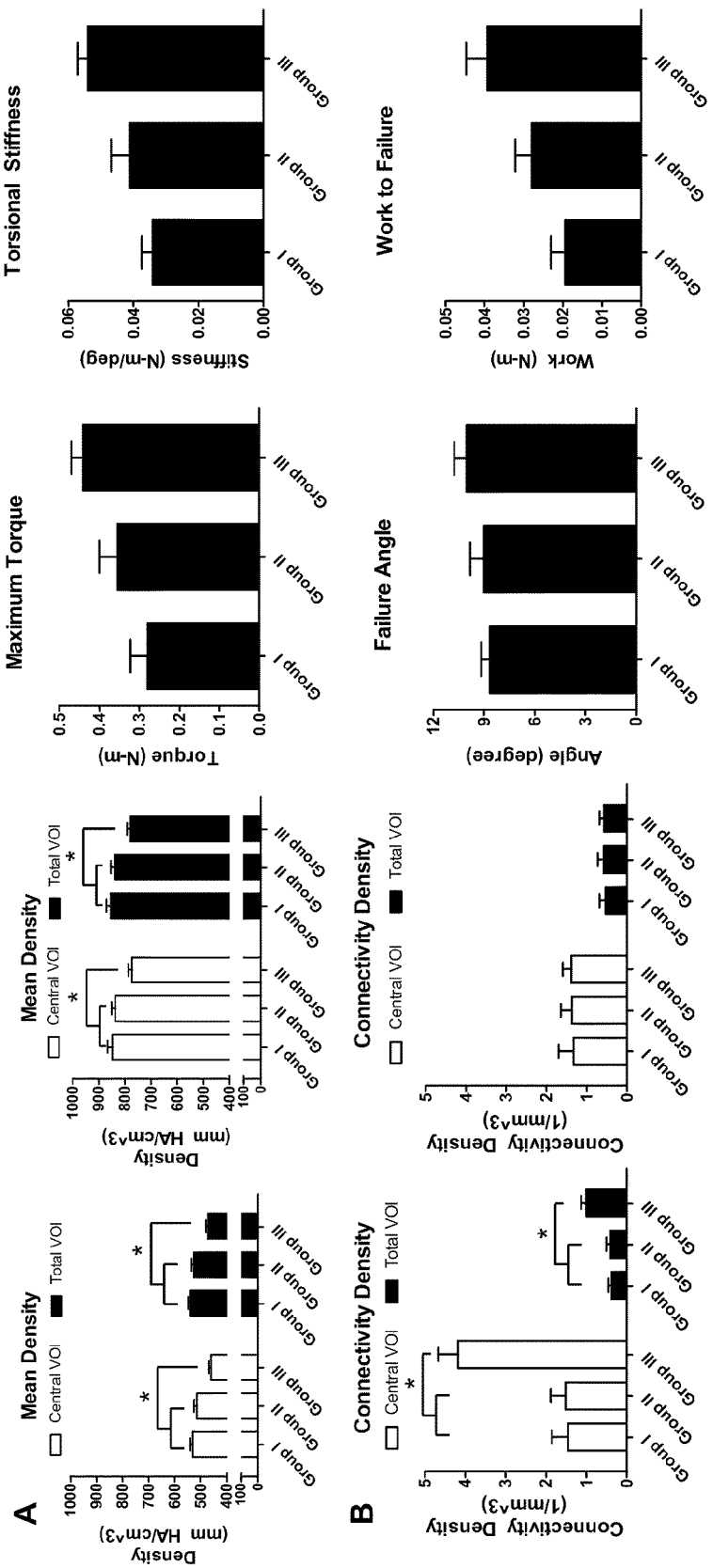
FIG. 31 illustrates the biomechanical properties of regenerated femurs at 12 weeks. (* indicates significantly different ($p<0.05$)).

Biomechanical properties. Biomechanical properties of the regenerated femurs were obtained from torsional testing at 12 weeks. The maximum torque was 58% higher for Group III (alginate+mesh) specimens, compared to Group I (collagen) specimens (FIG. 31). In addition, the torsional stiffness and work to failure of Group III specimens were significantly higher than those in Group I by 58% and 102%, respectively. Though the value of mean failure angle was largest in the case of Group III, there were no significant differences between the groups Importantly, there were no differences in the biomechanical properties between Groups I (collagen) and II (alginate). There were no significant differences in any of the mechanical parameters between Groups II and III; however the mean values of all parameters were higher for Group III specimens.

Discussion. This Example quantitatively compares a novel hybrid BMP delivery system to the current clinical standard for challenging bone defect repair. Compared to delivery on a collagen matrix, rhBMP-2 delivered at the same dose via alginate hydrogel resulted in enhanced bone formation as early as four weeks. The addition of a perforated nanofiber mesh to spatially retain the BMP hydrogel resulted in an increased mineral accumulation between 4 and 12 weeks, leading to enhanced bone ingrowth into the defect region at 12 weeks, compared to all other groups. Finally, biomechanical function was significantly improved following treatment with the hybrid nanofiber mesh/hydrogel delivery system, compared to collagen matrix delivery.

The amount and distribution of newly formed bone was influenced by the BMP delivery method. At two weeks, there appeared to a greater amount of mineral deposition with the collagen matrix delivery (Group I), compared to the alginate delivery (Groups II and III). However, by 4 weeks, the alginate groups demonstrated higher bone volume than the collagen matrix delivery, and this trend continued at 12 weeks. These results indicate that the kinetics of bone repair is dependent on the delivery system. This suggests that, whereas a majority of rhBMP-2 was released from the collagen matrix by 2 weeks, protein retention at the defect site beyond 2 weeks was improved with alginate hydrogel delivery. This is consistent with other studies that report that less than 5% of rhBMP-2 is retained within a collagen sponge by 2 weeks in vivo. Addition of the nanofiber mesh tube to the alginate hydrogel did not enhance overall bone formation that was seen in the total VOI. However, the pattern of bone formation that was observed in the alginate group without the mesh tube (Group II) indicated substantial bone formation outside the defect region, which implies leakage of the hydrogel and/or protein to the surrounding area. Analysis of the central VOI, which excluded this abnormal bone formation, revealed that presence of the nanofiber mesh tube (Group III) indeed enhanced bone formation within the defect region. This indicates that the nanofiber mesh tube is able to improve the spatial retention of rhBMP-2 within the defect by containing the alginate and/or the growth factor.

Differences due to the BMP delivery method were observed in mineral deposition rate, as well as mineral density and biomechanical properties of the regenerated bone. Mineral accumulation between 4 and 12 weeks was highest for specimens in the hybrid delivery group (Group III), even higher than the alginate group without the mesh tube (Group II). This suggests that presence of the nanofiber mesh tube improves localization of rhBMP-2 within the defect site for a longer time period. It is possible that the nanofiber mesh tube slows the protein diffusion away from the implant, by perhaps binding the protein through non-specific interactions. In an in vitro study, we observed that overnight incubation of a nanofiber mesh sample with a model protein, ovalbumin, resulted in 90% of the protein bound to the mesh, which remained attached to the mesh even at 1 week (data not shown). As the surface area of the nanofiber mesh is relatively large, these interaction effects may have a substantial effect on protein retention. Alternatively, the nanofiber mesh tube may function by constraining and therefore compacting the BMP-containing hydrogel, which could improve the local retention at later time points. In contrast to mineral accumulation, the density of the mineralized tissue was lowest in Group III. This suggests that new, immature bone is still being laid down in Group III specimens at later time points, which lowers the overall bone density in this group. It should be noted that the density obtained from the μCT is the actual density of the bone tissue, and not the apparent density of the entire bone. This would explain the lower tissue density in Group III specimens, even though the regenerated bone in these specimens appeared denser in the radiographs. In spite of the lower tissue density, maximum torque, torsional stiffness and work to failure were significantly higher in Group III specimens, when compared to those in Group I. This indicates that the higher bone volume in Group III compensated for the lower mineral density in contributing to the biomechanical properties. It should be noted that the Group III torsional properties exceeded those of age-matched intact femurs determined previously (Chapter 5). For example, the mean maximum torque of Group III samples was observed to be 0.44 Nm, whereas it was 0.31 Nm in the case of intact femurs. There were no significant differences in the biomechanical properties between Groups II and III; however the mean values were consistently higher for Group III specimens. This suggests that, although there was significantly higher mineralization in Group III inside the defect region, the bony tissue outside the defect in Group II contributed somewhat to the overall mechanical properties.

The connectivity of the regenerating bone was also affected by the protein delivery system. Connectivity density is a parameter used to analyze trabecular bone, and is a measure of the number of trabeculae in a unit volume. Though regenerating bone does not consist of mature trabeculae, the direct mineralization induced by BMPs is initiated at discrete locations, which then develop connections as the mineralization progresses. The connectivity obtained from the μCT analysis of regenerating bone is a measure of these connections. At 4 weeks, Group III specimens demonstrated the highest connectivity density, compared to the other two groups, indicating a more interconnected bone structure, perhaps because of the spatial guidance provided by the alginate hydrogel and the containment effect of the nanofiber mesh tube. Containment due to the mesh tube may have facilitated connection of the mineralized nodes formed during intramembranous ossification. There were no differences in connectivity density at 12 weeks, and the values were uniformly low. This could be due to the fact that as the defect fills with bony tissue, the discrete bone initiation centers merge to form a continuous volume, which would reduce the connectivity density.

The results of this Example demonstrate that delivery of rhBMP-2 via the hybrid nanofiber mesh/alginate system results in improved bone repair compared to delivery on a collagen matrix, the technique currently used by orthopaedic surgeons. Delivery of BMPs on collagen matrix has been shown to result in significant initial burst release, in the range of 40-90%. In the in vitro release of Example 3, approximately 10% of the encapsulated rhBMP-2 remains attached to alginate after 3 weeks, though the amount released in the media was negligible at this time point. This suggests that the protein binds to the alginate matrix and may be available to invading progenitor cells at later time points, which would mean that the function of the alginate hydrogel is more to improve long term availability than sustained release. Binding of the protein by alginate may be advantageous by protecting it from degradation. These results also suggest that the nanofiber mesh tube may aid in containing the exogenous growth factor within the defect region.

The delivery of BMPs on collagen matrix has been tested in a number of animal models of large bone defect repair; however high protein doses are typically required. For instance, it has been reported that delivery of 10 μg rhBMP-2 (double the dose used in this study) resulted in bony bridging of a 6 mm rat segmental defect, which is less challenging than the 8 mm defect utilized in this Example. The injection of 5 μg rhBMP-2 in this Example is equivalent to a 20 μg/kg dose, which is around $\frac{1}{5}^{th}$ the clinical dose used in humans. It should be noted that sensitivity to rhBMP-2 varies with species; however our dose is still low compared to that used in similar models. By maintaining sustained and localized availability of rhBMP-2, the hybrid alginate/nanofiber mesh system could result in functional bone restoration at a lower dose, thereby reducing the cost and complications associated with collagen matrix delivery. In conclusion, this study provides promising evidence in a challenging small animal model that spatiotemporal delivery strategies may enhance the therapeutic efficacy of BMP for repair of large bone defects.

What is claimed is:

1. A system for affecting an anatomical structure having a fillable space, the system comprising
a nanofiber mesh configured to substantially conform to an external surface of the anatomical structure, wherein at least a portion of the nanofiber mesh delineates a boundary between a milieu surrounding the anatomical structure and the fillable space of the anatomical structure and further comprising an injectible, flowable carrier substance substantially filling the fillable space of the anatomical structure.

2. The system for affecting an anatomical structure of claim 1, further comprising an active agent.

3. The system for affecting an anatomical structure of claim 1, wherein the nanofiber mesh has an average pore size of less than about 100 micrometers.

4. The system for affecting an anatomical structure of claim 1, wherein the nanofiber mesh further comprises a plurality of macropores.

5. The system for affecting an anatomical structure of claim 2, wherein the active agent comprises at least one member of the transforming growth factor beta superfamily.

6. The system for affecting an anatomical structure of claim 5, wherein the carrier substance comprises a hydrogel.

7. The system for affecting an anatomical structure of claim 6, wherein the anatomical structure is bone, and wherein the carrier substance comprises alginate or a derivative thereof, and wherein the at least one member of the transforming growth factor beta superfamily comprises a bone morphogenetic protein.

8. The system for affecting an anatomical structure of claim 7, wherein the active agent further comprises a plurality of mesenchymal progenitor cells.

9. A kit for affecting an anatomical structure having a fillable space, the kit comprising:
a nanofiber mesh configured to substantially conform to an external surface of the anatomical structure, wherein at least a portion of the nanofiber mesh delineates a boundary between a milieu surrounding the anatomical structure and the fillable space of the anatomical structure; and
a flowable hydrogel system comprising at least one active agent, wherein the flowable hydrogel system is injected into and substantially fills the fillable space of the anatomical structure.

10. The kit for affecting an anatomical structure of claim 9, wherein the nanofiber mesh has an average pore size of less than about 100 micrometers.

11. The kit for affecting an anatomical structure of claim 10, wherein the nanofiber mesh further comprises a plurality of macropores.

12. The kit for affecting an anatomical structure of claim 10, wherein the anatomical structure is bone, and wherein the flowable hydrogel comprises alginate or a derivative thereof, and wherein the active agent comprises a bone morphogenetic protein.

* * * * *